(12) United States Patent
August

(10) Patent No.: US 6,641,522 B2
(45) Date of Patent: *Nov. 4, 2003

(54) METHOD AND APPARATUS FOR BIOPHILICALLY PROMOTING PERSONAL RELAXATION, FOR REDUCING PHYSICAL AND/OR PSYCHOLOGICAL PERSONAL STRESS AND FOR EXPEDITING PERSONAL RECOVERY

(76) Inventor: Joseph August, 146 Spencer Rd., Woodstock, NY (US) 12498

(*) Notice: Subject to any disclaimer, the term of this patent is extended or adjusted under 35 U.S.C. 154(b) by 0 days.

This patent is subject to a terminal disclaimer.

(21) Appl. No.: 09/898,665

(22) Filed: Jul. 3, 2001

(65) Prior Publication Data

US 2002/0038073 A1 Mar. 28, 2002

Related U.S. Application Data

(63) Continuation of application No. 08/949,215, filed on Oct. 10, 1997, now Pat. No. 6,254,527, which is a continuation-in-part of application No. 08/583,473, filed on Jan. 5, 1996, now Pat. No. 5,681,259, and a continuation-in-part of application No. 08/644,473, filed on May 10, 1996, now Pat. No. 5,676,633.

(51) Int. Cl.$^7$ ............................................. A61M 21/00
(52) U.S. Cl. ............................. 600/27; 600/26; 160/10
(58) Field of Search ............................ 600/26, 27, 28; 40/421, 800, 904; 248/441.1, 457, 469; 261/DIG. 14

(56) References Cited

U.S. PATENT DOCUMENTS

| | | | | | |
|---|---|---|---|---|---|
| 4,763,428 A | * | 8/1988 | Fischer | ......................... | 40/712 |
| 5,304,112 A | * | 4/1994 | Mrklas et al. | ................. | 600/27 |
| 6,254,527 B1 | * | 7/2001 | August | ......................... | 600/27 |

* cited by examiner

Primary Examiner—Rosiland S. Kearney
(74) Attorney, Agent, or Firm—Alfred M. Walker

(57) ABSTRACT

A method and apparatus for relaxing a person in a stressful environment, such as a health care, business, hospitality or educational setting, provides a person with a choice of selecting for viewing one or more high resolution spatially open, serene natural landscape scenes to which the person is believed to have an innate positive (biophilic) affinity, upon a fabric frame display member mounted upon a flexible wall partition, such as a hospital curtain, a ceiling, a stand or other display member. In one embodiment, the spatially open, serene natural landscape scene is a savanna-type landscape or a like scene to which humans are believed to have a biophilic affinity. The biophilic landscape picture is printed preferably on a flexible fabric by a high resolution sublimation printing process, wherein an image is first scanned into a computer and then transformed by state-of-the-art technology to the fabric herein. The image may also be printed directly on all or a portion of a curtain itself.

21 Claims, 21 Drawing Sheets

FIG. 13
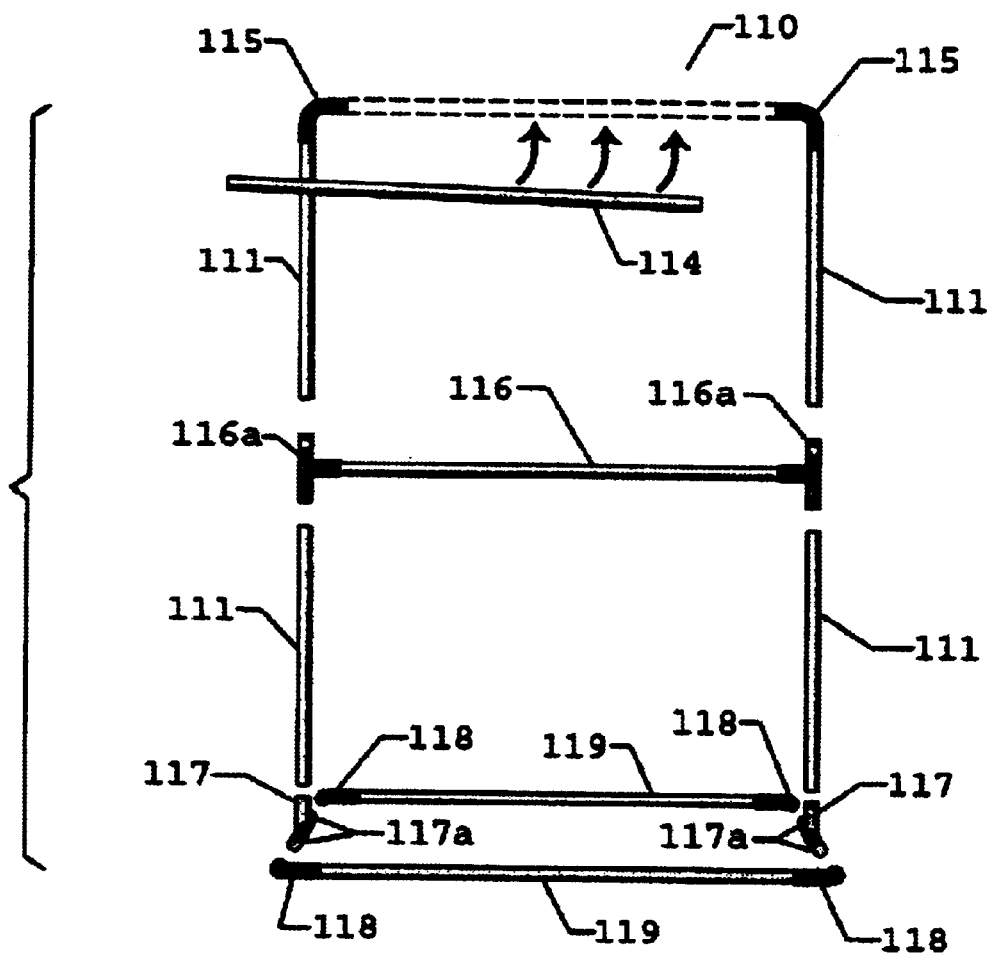
FIG. 13A
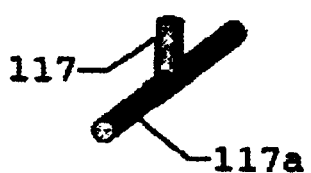
FIG. 13B
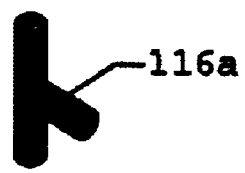
FIG. 13C
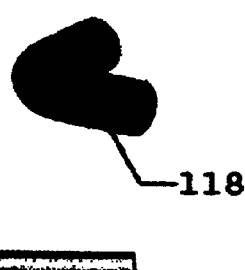
FIG. 13D

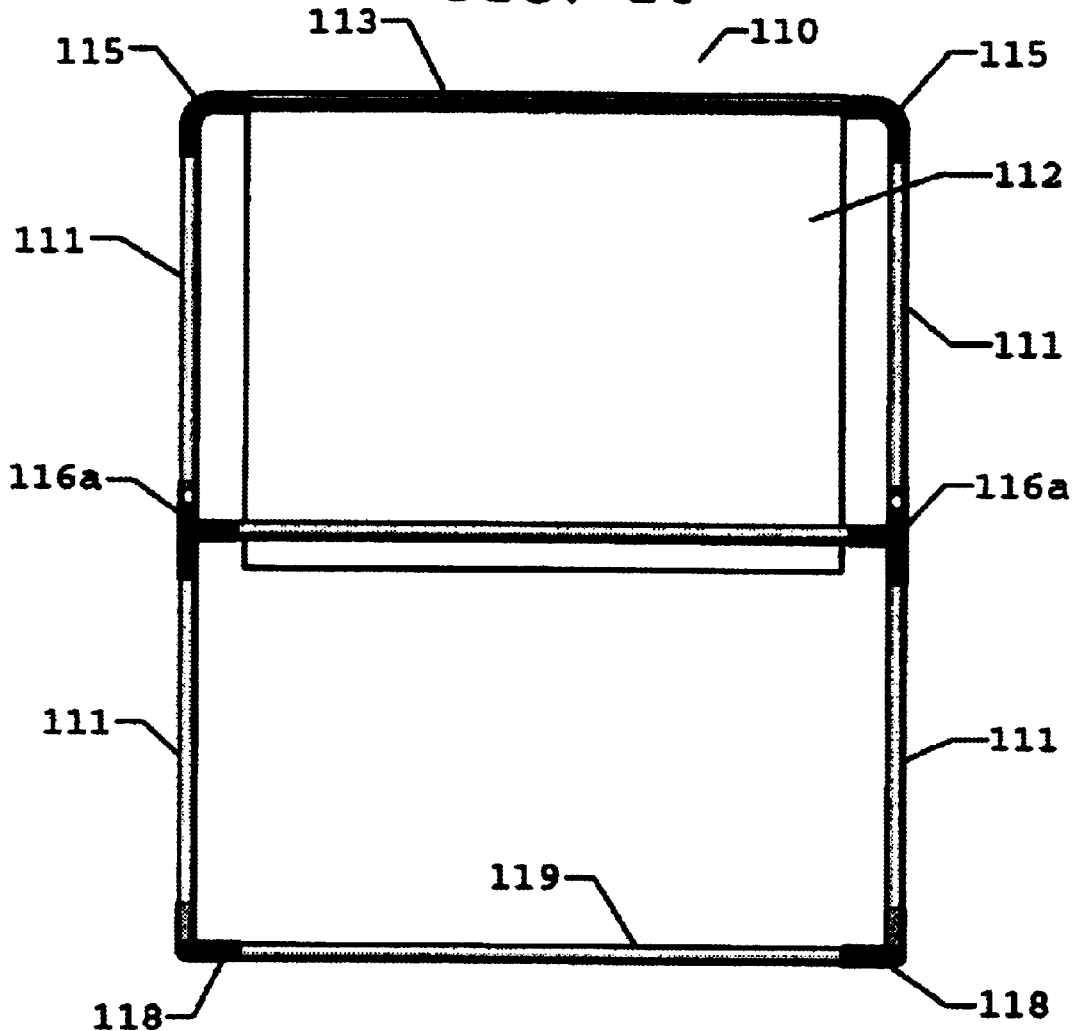

METHOD AND APPARATUS FOR BIOPHILICALLY PROMOTING PERSONAL RELAXATION, FOR REDUCING PHYSICAL AND/OR PSYCHOLOGICAL PERSONAL STRESS AND FOR EXPEDITING PERSONAL RECOVERY

This application is a continuation of application Ser. No. 08/949,215, filed Oct. 10, 1997, U.S. Pat. No. 6,254,527, and which application is a continuation-in-part of application Ser. No. 08/583,473 filed Jan. 5, 1996, now U.S. Pat. No. 5,681,259, and of application Ser. No. 08/644,473, filed May 10, 1996, now U.S. Pat. No. 5,676,633.

FIELD OF THE INVENTION

The present invention relates generally to the field of methods and devices for promoting personal stress reduction and relaxation; more particularly, the present invention concerns methods and apparatuses used to expose persons to appropriately selected visual stimuli which promote relaxation in intimate settings, such as in hospital room environments, office cubicles, health care institutions, educational institutions, and hospitality accommodations, or other like settings.

BACKGROUND OF THE INVENTION

Positive psychological and physiological responses are elicited in humans by visual exposure to pleasing landscape images such as pictures of spatially open natural landscapes. (Roger S. Ulrich, 1993, "Biophilia, Biophobia and Natural Landscapes", Chapter 3, pages 73 to 137, in: Stephen R. Kellert and Edward O. Wilson editors, *The Biophilia Hypothesis*, Island Press, Washington, D.C.) The preferred landscape image is a savanna-type landscape. By definition, a savanna-type landscape is a "grassland with scattered trees or scattered clumps of trees, a type of community intermediate between grassland and forest" (Eugene P. Odum, 1971, *Fundamentals of Ecology, Third Edition*, W. B. Saunders Company, Philadelphia, Pa.).

In one of his seminal and theoretical works, renowned evolutionary biologist Edward 0. Wilson (1984), *Biophilia: The Human Bond with Other Species*, Harvard University Press, Cambridge, Mass.) suggests that humans are genetically predisposed to respond positively (biophilically) to savanna-like landscapes. After the publication of Wilson's seminal work on island biogeography (Robert H. MacArthur and Edward 0. Wilson, 1967, *The Theory of Island Biogeography*, Princeton University Press, Princeton, N.J.) and his expansive synthesis on sociobiology (Edward 0. Wilson, 1975, *Sociobiology: The New Synthesis*, Harvard University Press, Cambridge, Mass.), biologists and others wrote many papers, dissertations and books on these topics of modern bioscience. Like the responses by the bioscientific community to his 1967 and 1975 works, Wilson's 1984 publication of *Biophilia: The Human Bond with Other Species* has prompted the writing of many scientific papers by a wide diversity of authorities. Among these works on biophilia are two papers especially relevant to the present invention: the aforecited "Biophilia, Biophobia and Natural Landscapes" by Ulrich, and "Humans, Habitats, and Aesthetics" by Judith H. Heerwagen and Gordon H. Orians (1993, Chapter 4, pages 138–172, in Stephen R. Kellert and Edward 0. Wilson, editors, *The Biophilia Hypothesis*, Island Press, Washington, D.C.).

The biophilic theory of Wilson supports the belief that natural selection favored the survival of paleohominids (ancestors of modern humans, *Homo sapiens*) genetically predisposed to inhabiting landscapes dominated by plant life forming vegetation having a physiognomy of a savanna. Such ancestral hominids are viewed as having innate aversions to desert, densely forested and like landscapes-generally less favorable to paleohominid survival than savannas. Human evolution is believed to have occurred substantially within tropical savannas in Africa. Predation, food-availability and other selection pressures were generally more favorable to human survival and evolution within these tropical savannas than in other kinds of African landscapes (such as tropical rain forest, mountainous, desert and like environments). Selection promoted disproportionately high survival of hominids and hominid genes favoring savanna-oriented behaviors. As evolution proceeded, there was a build-up and strengthening of genes and gene-combinations further predisposing hominid populations to savanna conditions. Wilson believes that these innate savanna-oriented characteristics continue in populations of modern humans and that modern humans are biophilically predisposed to responding favorably to savanna or savanna-like conditions. Certain embodiments of the present invention are in accord with this belief of one of the most widely respected and acclaimed biologists in the world today.

In the aforementioned 1993 publication of Ulrich, Ulrich reports evidence that simulations (including color photographs) of natural environments elicit restorative and other positive responses from human viewers and suggests that such simulations may serve as at least partial substitutes for real nature in terms of eliciting short-term restorative responses. Other scientific authorities are mentioned by Ulrich as providing proof that the viewing of natural settings positively affects the viewer by reducing stress (confirmed by such central nervous system indicators as blood pressure). This reporting by Ulrich is consistent with the innate biophilic landscape affinity believed by Wilson to characterize modern humans. The work of Ulrich suggests that positive (biophilic) responses can be elicited from patients within a very short time after patient exposure to wall art showing spatially open serene natural settings.

However, most attempts to reduce stress in a hospital or therapeutic setting have been sound-oriented, wherein music or other sounds are electronically delivered to a patient, where visual images are used to address patient well being, the images are either displayed remotely in a far away picture frame, or in optically glare-producing video screens.

Among the earlier background art patents related to methods of patient recovery stress reduction or promoting relaxation are the following:

| U.S. Pat. No. | Inventor |
|---|---|
| 3,140,709 | Weisz |
| 3,642,941 | Kashar |
| 3,773,049 | Rabichev et al. |
| 3,826,250 | Adams |
| 4,047,377 | Banks |
| 4,082,918 | Chang et al. |
| 4,124,022 | Gross |
| 4,553,534 | Stiegler |
| 4,573,449 | Warnke |
| 4,640,267 | Lawson |
| 4,681,096 | Cuervo |
| 4,762,131 | Okuda |
| 4,763,428 | Fischer |
| 5,219,322 | Weathers |
| 5,266,070 | Hagiwara |

-continued

| U.S. Pat. No. | Inventor |
|---|---|
| 5,267,942 | Saperston |
| 5,289,438 | Gall |
| 5,296,444 | Saiki et al |
| 5,304,112 | Mrklas |
| 5,352,181 | Davis |
| 5,356,368 | Monroe et al |
| 5,377,024 | Dillinger |
| 5,403,263 | Rodgers |
| 5,425,699 | Spiegel |
| 5,433,223 | Moore |

The most relevant patents are U.S. Pat. No. 5,403,263 of Rodgers, for a method of reducing the recovery time and stress associated with surgery and U.S. Pat. No. 4,763,428 of Fischer for providing a nature scene in a hospital wall-mounted picture frame. Rodgers '263 describes a method to reduce hospital recovery time and stress by providing verbal voice-over suggestions and soothing anxiolytic music before, during and after surgery. Fischer '428 describes the use of wall mounted pictures to assist in patient healing, but does not focus on what pictures to select other than nature scenes in general.

Weathers (U.S. Pat. No. 5,219,322) describes a reclining chair for a medical patient who is hooked up to an electronic apparatus for the controlled presentation of visual and auditory stimuli. Similarly, Mrklas (U.S. Pat. No. 5,304,112) describes a system where a patient is put in a chair in front of an electronic screen and is exposed to electronic visual images, auditory sounds and other stimuli.

Weisz (U.S. Pat. No. 3,140,709) describes a pain relieving apparatus wherein acoustical sounds such as music are fed through ear phones to divert a patient's attention from pain.

Rabichev et al. (U.S. Pat. No. 3,773,049) describe an electronic apparatus for treating neuropsychic and somatic disorders with repetitive exposure of the patient to light, heat and sound radiation sources.

Banks (U.S. Pat. No. 4,047,377) discloses an electronic sleep promotion apparatus wherein a wide band audio frequency generator applies audio impulses to a person.

Chang et al. (U.S. Pat. No. 4,082,918) describe an electronic audio device which provides analgesic sounds to dental patients.

Gross (U.S. Pat. No. 4,124,022) describes an electronic audio speaker in the shape of a heart, which provides repetitive slow heartbeat sounds, to relax a person.

Kashar (U.S. Pat. No. 3,643,941) describes a relaxation chamber containing a plurality of Styrofoam® balls to simulate movement of a person within a swimming pool. Colored lights are projected upon the Styrofoam® balls to enhance the person's relaxation.

Adams (U.S. Pat. No. 3,826,250) discloses a relaxation chamber including a lounge chair wherein lights and sounds are electronically provided to a resting person.

Steigler (U.S. Pat. No. 4,553,534) describes a stress-reducing helmet with an eye shield, wherein electronic images and sounds are transmitted to the wearer.

Warnke (U.S. Pat. No. 4,573,449) describes a method for sleep enhancement and/or relaxation wherein a headphone generates electronic sound pulses, which are provided to an insomniac person to induce sleep.

Lawson (U.S. Pat. No. 4,640,267) and Cuervo (U.S. Pat. No. 4,681,096) both describe methods and associated devices to abate an infant's crying, wherein electronic sounds or vibrations are scheduled for repetitive introduction to the infant.

Gall (U.S. Pat. No. 5,289,438) discloses a consciousness-altering apparatus for persons, wherein multiple sound stimuli are electronically provided to a person.

Monroe (U.S. Pat. No. 5,356,368) describes a method and apparatus for altering consciousness and inducing sleep by measuring electroencephalogram (EEG) brain wave forms of a person during sleep or relaxation, and using sounds to try and reproduce the sleep inducing or relaxation-inducing brain waves of the person.

Dillinger (U.S. Pat. No. 5,377,024) describes an electronic color forming image construction device.

Spiegel (U.S. Pat. No. 5,425,699) describes the use of electronically produced sound waves to induce hypnosis in a person.

Okuda (U.S. Pat. No. 4,762,131) discloses an electronic nerve stimulation including lights and sounds to treat paralytic patients.

Monroe et al. (U.S. Pat. No. 5,356,368) describe a method for predicting when a night-shift worker might lose alertness.

Saperston (U.S. Pat. No. 5,267,942) discloses the use of electronically generated sounds to monitor optimal target heart rates in persons.

Davis (U.S. Pat. No. 5,352,181) describes a method and apparatus for inducing relaxation by providing verbal and musical sounds in ascending and descending crescendos and phases, to stimulate relaxing alpha and beta brain waves.

However, Rodgers '263 and most of the above noted background art patents are directed to electronic sound generating devices to induce relaxation states in users. Some of these devices, such as the embodiments of Okuda is '131 and Kashar '941, involve the use of electronically generated flashing lights to induce relaxing states of mind.

Furthermore, providing such a repetitive exposure of a patient to music, sounds and/or flashing lights has the disadvantage of being expensive to install and also may overstimulate the patient.

Moreover, these background art devices do not describe a method and apparatus for providing biophilic landscape images to persons to promote stress reduction in various stress-filled environments, such as hospital rooms, office cubicles, health care settings or educational institutions.

Furthermore, the hospital room environment itself has the disadvantage of discouraging exposure of persons to pictures in general, because slidable fabric curtains are often drawn around the patient's article of furniture thereby hiding any wall-mounted pictures, such as described in U.S. Pat. No. 4,763,428 of Fisher, from the patient's view.

Fischer also discloses in an unpatented publication entitled "Visual Therapy" the displaying of one of many nature photography scenes in a light box or a lighted electronic video screen in a health care setting. However, the lighted images are subject to optical glare.

The background art of Fischer '428 and the Fischer "Visual Therapy" publication of visually oriented approaches to patient well being is aimed primarily at providing either a reusable lockable means, such as a picture frame, or a light box or video screen, to display pictures that are only generally described as "having a therapeutic value", and "particularly well suited to visually involve, distract and occupy the attention of the viewer" of nature photography on the hospital room wall. There is no specificity as to the theoretical basis for selection of the nature photography; nor are any selection guidelines presented.

While a hospital curtain exhibits a large, convenient surface upon which to display pictures, curtains have not been generally used to display framed pictures, because the weight of a picture frame may distort the curtain and/or because the rigid picture frame may be a hazardous hindrance obstructing egress in the vicinity of the curtain. In addition, light boxes and lighted video screens present other electricity related hazards.

Therefore, there is a need for a lightweight, flexible display means for pictures, which can be displayed on a stand or can be attached to a hospital curtain without distorting the curtain and without obstructing egress to the patient in the vicinity of the curtain.

In fact, flexible removable pictures have mainly been provided within infant cribs to protect an infant's safety, as noted in U. S. Pat. Nos. 5,307,574 and 5,125,175 of Huff.

Moreover, imprinted photographic pictures cannot normally be displayed on fabrics, such as curtains, because the images fade with repeated washing of the fabric materials.

The technical challenges in providing such cubicle curtain-mounted images include: (1) Any fabric that is used must either be inherently fire retardant or specially topically treated to meet the fire retardancy standards as set forth in National Fire Protection Association (i.e., NFPA) Code 701. (2) The printing must produce images of sufficient high-resolution photo-realism and sufficient size (e.g., four by five feet) to give the person, such as a hospital patient, the perception of actually being in a natural (i.e., biophilic-like) setting. (3) The photo-realistic image must be printed on inherently fire retardant or treated fabric, in a manner that upholds the post-printing fire retardancy of the fabric and in a manner that enables the fabric to be laundered and disinfected at the high water and drying temperatures required by hospital sanitary codes and standards while maintaining the image quality of the picture.

High resolution, non-fading printing of photographic images on cloth fabrics may be obtained by special printing processes, such as, for example, sublimation printing. Sublimation printing produces images which have high image resolution with much clarity and brilliance, without the visually disturbing effects of glare produced by light boxes or electronic screens, such as described in the Fischer "Visual Therapy" publication.

Among the background art describing sublimation printing include U.S. Pat. No. 5,460,871 of Andersen, U.S. Pat. No. 5,441,997 of Walsh, U.S. Pat. No. 5,389,493 of Asai, U.S. Pat. No. 5,329,381 of Payne, U.S. Pat. No. 4,997,506 of Recher, and U.S. Pat. No. 4,804,977 of Long.

In sublimation printing, the coloring agents are subliminally transferred to the fabric. Sublimation printers use sublimation powders or printer ribbons to produce heat transfers, which release sublimation inks in a wide variety of distinctive colors, as noted in U.S. Pat. No. 5,281,499 of Bussard.

Since the resolution quality is achieved with photographic images printed on fabrics by sublimation printing, the fabrics can therefore be fire retardant and washable, so that the fabrics can be laundered and disinfected when washed at high water temperatures with cleaning products.

Reusable fabrics are also much easier to clean and maintain than complicated light boxes or electronic video screens, and are more easily interchangeable than heavy, wall mounted-picture frames.

Therefore, the high water temperatures and cleaning products (which are needed to bring fabrics up to hospital and other sanitary codes,) do not substantially diminish the high resolution and clarity of photographic images produced by sublimation printing upon a fabric, such as hospital curtain material or another suitable fabric attachable to a hospital curtain. Moreover, these cleaning methods do not diminish the fire retardancy of the inherently fire retardant fabric.

OBJECTS OF THE INVENTION

Accordingly, an object of the present invention is to provide a method for visually and biophilically promoting personal relaxation, such as for a medical patient, before, during and/or after medical is procedures, such as surgery or diagnostic testing.

It is also an object of the invention is to provide a method for visually and biophilically reducing physical and/or psychological stress, promoting patient relaxation and expediting recovery in a patient before, during and/or after surgical or medical procedures in a hospital, medical or convalescent setting.

Another object of the invention is to provide a method for visually and biophilically expediting recovery of a medical and/or surgical patient.

A further object of the invention is to provide a method for visually and biophilically promoting surgical patient welfare in a hospital, medical institutional or convalescent setting, or a like environment.

A still further object of the invention is to provide a method for visually exposing a person, such as a medical patient to biophilic savanna-like scenes as biophilic stimuli before, during and/or after surgery and other medical procedures to promote relaxation, reduce patient stress and expedite patient recovery.

A yet further object of the invention is to provide a method which supplements visual biophilic stimuli with sound, aromatic and/or other stimuli for promoting medical patient relaxation, reducing patient stress and expediting patient recovery.

It is yet also an object of the present invention to provide a convenient changeable visual display means for displaying one or more biophilic pictures for which a predetermined patient has a biophilic affinity, in a facility associated with a stressful environmental, such as in a facility for the performance of diagnostic, treatment or surgical procedures, or in rehabilitation and convalescent settings.

It is a further object to provide such a visual display means to visually expose a patient to one or more biophilic pictures before, and/or after performance of surgery or other procedures on the patient.

It is also an object to provide a means for patient choice in selecting a visual display; such choice promotes the patient's self-efficacy, which thereby reduces stress and which promotes health and well being.

It is yet a further object to provide a person with a visual display means with one or more biophilic pictures as biophilic stimuli for promoting personal relaxation, for reducing physical and/or psychological stress, and, for persons in a hospital setting, for expediting recovery time.

It is yet another object of the present invention to augment the foregoing visual exposure of persons to biophilic scenes by providing sound recordings conducive to causing patient relaxation.

It is a further object of the present invention to further augment the foregoing visual exposure of persons to biophilic scenes by also providing therapeutic aromatic materials to the patient.

It is yet another object to provide a method of promoting patient recovery while the patient is in a hospital bed by displaying the biophilic pictures on a structural surface such as upon a ceiling, upon a self-standing support stand or upon a vertically draped curtain substantially near the article of furniture, wherein the picture is positioned to allow the patient to readily and comfortably view the biophilic picture.

It is yet another object to improve over the disadvantages of the background art directed toward complicated electronic sound-oriented relaxation devices for surgical, medical and other patients.

It is yet another object to improve over the disadvantages of the background art directed toward expensive, optical glare-producing lighted electronic screen displays of pictures.

It is yet another object to improve over the disadvantages of the prior art.

SUMMARY OF THE INVENTION

In keeping with these objects and others which may become apparent, the present invention provides a method of relaxing a person in a stressful environment, such as a patient in a health care, hospital or convalescent setting, by providing a person with a choice of selecting for viewing one or more high resolution spatially open, serene natural pictorial landscape scenes to which the person is believed to have an innate positive (biophilic) affinity, upon a conveniently viewable display, such as a ceiling mounted surface or upon a fabric frame display member mounted upon a flexible wall partition, such as a hospital curtain. In one embodiment, the spatially open, serene natural landscape scene is a savanna-type landscape or a like scene to which humans are believed to have a biophilic affinity.

A biophilic landscape picture of the present invention is printed preferably on a flexible fabric by a high resolution sublimation printing process, wherein an image is first scanned into a computer and then transformed by state-of-the-art technology to the fabric, such as described in the "Background of the Invention" herein. The image may also be printed directly on all or a portion of a hospital curtain itself.

Because of institutional safety requirements, such as hospital safety protocol and safety codes (i.e., what is referred to as "National Fire Protection Association (NFPA) 70111 codes), the display member, such as a fabric, must either be inherently flame retardant or specially treated to meet protocol or code requirements.

Moreover, in accord with hospital sanitary protocol, the fabric sheet pieces and inks thereon should be washable and durable to heated washing standards of 160° F. so that any infectious organisms thereon are eradicated.

The printing produces substantially glare-free photorealistic images of sufficient size (e.g. four by five feet) to give the person, such as a hospital patient, the perception of actually being in a natural (i.e., biophilic) setting. Printing the photo-realistic image is accomplished on inherently fire retardant or treated fabric in a manner that upholds the post-printing fire retardancy of the fabric and that enables the fabric to be laundered and disinfected at the required high water and drying temperatures required by hospital sanitary codes and standards without substantially degrading the image quality of the picture.

In order to display the visual display member, on a reverse side of the fabric one or more fastening means, such as strips of hook-and-loop-type fasteners, sold under the trade name of VELCRO®, are attached.

Corresponding strips of hook-and-loop type fasteners are attached to a portion of a wall support, such as a hospital room curtain, which at least partly encloses a hospital patient's bed.

Other conventional fasteners such as snaps, safety pins, clips, etc., may be substituted or additionally employed, such as curtain rod hooks which fit into eyelet grommets in a mesh flange above the image bearing fabric, so that the visual display member may be displayed from the curtain rod.

In the curtain mounted environment, by attaching the fabric picture to the patient-facing side of the hospital curtain, the biophilic landscape picture can remain visible to the targeted patient in the bed even when the curtain is contracted.

During visiting hours, when the curtain is normally partially expanded, the landscape picture can be left visible on a portion of the curtain.

Preferably, the picture should be attached so that it is visible at the foot of the patient's bed, within the patient's line of vision.

In conjunction with exposure of the person to the spatially open, serene natural landscape picture, the patient may be provided with soothing natural sounds appropriate to the landscape picture and/or mild-aromatic odors reminiscent of natural aromas associated with the landscape picture.

In selecting a spatially open, serene natural landscape for the patient to view, it is important that the person in a stressful environment, such as a medical patient, not be exposed to over-exciting or anxiety producing landscape scenes, (which may unconsciously raise the stress level of the patient and/or may affect the visual and auditory nerve balance mechanisms of the patient).

Therefore, selection of the biophilic visual image to be conveyed to the patient preferably encompasses selection of spatially open, serene landscape scenes which are substantially the same as, or similar to, the archetypal savanna-type landscape scenes, suggested by Ulrich, Wilson and other scientific authorities on biophilia.

The subjects of a biophilic scene, or other spatially open, serene, natural landscapes must be carefully chosen and the natural scenes should be selected in relation to the most recent relevant environmental psychology research (such as defined by Ulrich). Although pre-dating both the 1984 seminal work by Wilson and the subsequent 1993 publication of Ulrich, an example of environmental psychology methodology research on differential human perceptions of varying outdoor scenes is the 1974 work of Shafer and Richards entitled "A Comparison of Viewer Reactions to Outdoor Scenes and Photographs of These Scenes", (Shafer et al., 1974, *U.S. Dept. of Agriculture, Forest Service Research Paper No. NE*-302, Northeastern Forest Experiment Station, Forest Service, U.S.D.A., Upper Darby, Pa.)

In the Shafer and Richards study, eight different types of outdoor scenes were shown to viewers in three different modes: (i) on-site viewing of the actual scenes; (ii) viewing color transparencies of the scenes; and (iii) viewing color photographic prints of the scenes. Viewer responses to each scene were compared statistically and geographically to determine which outdoor scenes had more positive effects on the viewers.

Upon selection of the picture to be displayed to the patient, it should be conveniently displayed, such as on the hospital curtain, as noted before.

However, other embodiments of the present invention include other visual display means not previously described in this application. One such other kind of embodiment is a wall-or ceiling mountable, roll-up-able and roll-down-able screen depicting a spatially open, serene natural landscape scene (preferably a biophilic savanna-type scene).

Unlike the generalized nature photography described in Fischer '428 and the Fischer "Visual Therapy" publication, the present invention applies the latest research findings and theory in the behavioral and natural sciences to the selection and installation of appropriate nature photography scenes in stressful environments, such as hospital rooms and other settings, such as health care or educational institutions, hospitality accommodations, office cubicles or waiting rooms. It does so in a manner that creates a simulated natural environment to reduce stress and to promote the person's relaxation.

The selection of healing and recovery-promoting natural landscape scenes requires knowledge of the latest research findings concerning the health effects of viewing biophilic nature scenes, since not all natural landscape scenes have a therapeutic affect. In fact, uninformed, improper or inappropriate picture selection has been shown to have deleterious effects on patients, disturbing them rather than promoting their healing.

What is essential in the selection process is that the visual stimuli not merely tend to "involve, distract and occupy the attention of the viewer" but that such elicited patient responses promote the patient's healing and recovery. The present invention reflects an understanding of how to stimulate such viewer-based recovery responses because it is based on a firm foundation of the latest research findings and theoretical research focusing on the biophilic effects of viewing nature on human health outcomes. This research, by Wilson, Heerwagen, Orians, and Ulrich et al informs the user of the appropriate method of selection of recovery promoting biophilic natural landscape scenes.

Merely placing a picture on a wall, such as in a hospital room, whether in a frame, a light box or a video screen, is not sufficient to promote patient recovery. The Fischer '428 background art on hospital room walls is located at too remote a distance from the patient to promote the patient's perception of being in the environment represented by the picture. Moreover, while the Fischer "Visual Therapy" publication describes the lighted depiction of large photographs from light boxes or video screens, the light emitting features of the light boxes or video screens may produce stressful unwanted optical glare.

Furthermore, viewing of wall mounted light boxes and video screens can be obstructed by fabric hospital curtains drawn between a patient and a hospital room wall.

Therefore, one embodiment of the present invention is distinguished from the background art by providing very large sized high resolution photo realistic biophilic natural landscape scenes that, by being printed on flexible fabric, enable these scenes to be removably mounted on the patient's bedside cubicle privacy curtain in the patient's direct line-of-sight at the foot of the bed, thereby providing the patient with an immediately close-up simulated natural visual environment.

Since wall-mounted art described in the background art has the disadvantage of being obscured from the patient's view whenever the cubicle curtain is drawn to provide privacy to the patient, the patient is therefore caused to have to choose to either have personal privacy or to be able to view the wall-mounted photography.

With the above-described embodiment of the current invention, the patient no longer has to suffer the above described dilemma. It provides the person with an opportunity to choose one or more preselected biophilic scenes that, by virtue of their placement on the cubicle curtain, can be viewed at the discretion of the person any hour of the day or night without the glare of a video screen or the remoteness of a wall mounted frame. With the embodiment of the present invention the person is not forced to choose between having personal privacy or viewing wall-mounted nature photography.

On the contrary, with this embodiment of the present invention the person is able to enjoy the benefit of (or exercise the choice of having) personal privacy while simultaneously having the opportunity to view selected restorative biophilic nature photography.

An additional embodiment of the latter-described embodiment augments the visual dimension of the environment with complementary audio recordings of biophilic sounds appropriate and specific to each scene.

Still another embodiment augments the visual and audio stimuli with aromatic scents that are appropriate and specific to each scene.

Also, the method of the present invention may allow (after a set of spatially open serene natural landscape scenes is selected by the person's care giver) the person to select one or more of these scenes. This alternative variation permits patients to exercise choice, thereby improving the patient's self-efficacy and ultimate recovery. Moreover, the biophilic or other spatially open, natural serene landscape scenes may be visually displayed substantially glare-free in other medical or convalescent environments, such as in the offices of health practitioners, (e.g., physicians, dentists, acupuncturists, chiropractors, and physical therapists). Other appropriate settings include diagnostic rooms at hospitals, adult day care centers, other institutional settings and/or at an office or at a private residence (such as where an infirm person might be confined to a particular room for extending periods of time while recovering from illness or surgery).

In addition, the visual display may be supported upon a horizontal upper rod of a self standing support stand, which can be conveniently moved about a room. Alternately, the display may be upon a flat member and displayed upon one or more ceiling surfaces, to be seen by persons in a face up, supine position, such as lying upon a hospital gurney. A plurality of ceiling mounted images may be provided at intermittent ceiling positions along a corridor, so that a person lying face up upon a gurney can view a series of ceiling mounted images while being moved.

The grommet-mounted embodiment allows the visual display, such as a photomural, to be hung in direct view of the patient, using existing conventional hardware in the hospital or other healthcare facility room. It offers the facility two advantages over the VELCRO® mounted application:

1) it does not require any prior preparation of the existing curtain in order to receive this photomural e.g. no sewing of VELCRO®, 2) because the visual display, such as a photomural, is attached higher up and closer to the ceiling, it is less likely to be stolen.

Additional, in a portable stand-mounted embodiment, the visual display, such as a photomural is hung from a self-standing portable stand by inserting the stand's removable top horizontal piece through a sleeve which runs across the top of the visual display photomural.

The portable stand is placed in direct line of sight of the patient, usually at the foot of the patient's bed, gurney or recliner. Alternatively, for patients who are receiving chemotherapy, dialysis or other treatment where they are side by side with other patients, the portable stand can, by being placed at the patient's side, serve as a privacy screen between patients.

Additionally, auditory sounds can be played through a cassette or CD player or broadcast on a channel of an in-house television system.

The portable stand adds considerable flexibility of use for both institutional as well as home healthcare and home stress reduction applications.

For institutions, the portable stand allows the staff to utilize this biophilic environment for multiple patients on an "as needed" basis. The portable stand is lightweight and is easy for a single staff person to transport. This portability makes it easy, for example, for a staff person to bring it directly to a patient who is anxious and is having difficulty falling asleep in order to help relax that patient and, thereby, assist them in failing asleep.

The portable stand allows the institution to also flexibly respond to the needs of specific populations of patients. For example, it allows the staff to use it, as an early intervention, alternative to physical and pharmacological restraints, to distract and relax Alzheimer's patients who are exhibiting "catastrophic reactions".

The portable stand allows institutions to provide the stress reducing benefits of the biophilic environment in settings where there are no approximately located cubicle curtain tracks to hang it from, or where the position of the existing tracks is not ideal for optimal viewing by the patient, e.g. for bathing, hydrotherapy, occupational, physical therapy and other rehabilitation, intensive care (ICU's, CCU's), private rooms, waiting rooms, conference, meeting or quiet or meditative rooms for family/physicians conferences or personal reflection and repose), etc.

The stand may also be used in private residential homes for convalescence, long-term care, palliative (or hospice) care, treatment and general "well-person" stress reduction.

As with the institutional applications, the stand can be used in private residential homes to display biophilic and other therapeutic visual material specifically targeted to the needs of particular populations, e.g. Alzheimer's patients, depressed individuals (e.g. whose therapeutic needs may be for stimulation and inspiration) pediatrics patients, or healthy infants, to be used to stimulate the infant's cognitive development.

The portable stand-mounted biophilic visual display environment can also be used for business offices or hospitality accommodations, such as hotel rooms, and other public settings as a stress reduction environment, wherein it can be used in work areas, meeting rooms, cafeterias, employee lounges, etc.

Furthermore, in the settings enumerated above as well as waiting rooms of all types, the biophilic environment can alternatively be installed by mounting the visual display on a simple curtain rod attached to a wall or partition. The display, such as a photomural, is hung in this manner by sliding the rod through the sleeve across it's top. The sounds can be played through a cassette or CD player or broadcast on a channel of an in-house audiovisual system or other sound reproduction or transmittal system.

The biophilic images may alternatively be mounted on the ceiling above the patient. Such mounting can utilize simple tacks or other conventional devices.

This application allows patients whose diagnosis, treatment or convalescence requires them to be in a reclining position, to experience the therapeutic benefits of the biophilic environment.

This application is also for institutional and home healthcare/well care settings, offices, hospitality accommodations, work areas, employee lounges, waiting rooms, etc.

The biophilic environmental displays can promote stress reduction of employees and customers. These embodiments include:

a) photomurals printed on flexible textile fabric mounted on portable stands or walls, window shades, venetian blinds and other window treatments, augmented by recordings of ambient biophilic nature sounds (broadcast by on-site cassette or CD players or through a centralized-sound system) or other sound reproduction systems.

b) modular office dividers/cubicles with biophilic views in the employees' or waiting customers/clients' line of sight (i.e. above the desktops or tops of seating arrangements or along corridors created by such the modular dividers) with or without built-in (i.e. self-contained) ambient environmental sound devices.

Such sound devices are already on the market; however they are not being utilized in this manner.

Moreover, in biophilic ceiling panel healing environments, visual displays may also include ceiling panels. In this ceiling mounted embodiment, biophilic visual displays, such as photomurals, are attached to ceiling panels that fit into standard ceiling metal grids. They can be used as single panels or can used in multiples to simulate biophilic natural scenes on the ceiling of corridors so as to provide anxiety and stress reduction benefits to patients as they are transported through the hospital corridors. The sounds may be broadcast from a centralized source and heard in each location by means of ceiling or wall mounted speakers.

Patients are routinely transported through hospital corridors, going to and from diagnosis, treatment and surgery. These are usually times of intense anxiety and stress for the patients. These states of psychological distress have been shown to suppress immunological functioning and thereby hinder the patients' physiological recovery. The present invention provides patients with relief of this distress during these critical moments of transport.

These biophilic ceiling healing environments can alternatively be used on the ceilings of any healthcare setting e.g. patient rooms, procedure rooms, diagnostic rooms, emergency, operating rooms, etc. They may also be used in elevators.

In general, there are many display alternatives for displaying a biophilic visual display, such as a biophilic photomural, in the vicinity of persons in a stressful environment, such as in a hospital, medical waiting room, long term care institution, hospitality accommodation or office cubicle.

DESCRIPTION OF THE DRAWINGS

The present invention can best be understood in conjunction with the accompanying drawings, in which:

FIG. 13 is an exploded front perspective view of the mounting stand portion of the embodiment as in FIG. 9;

FIGS. 13A, 13B, 13C and 13D are close-up perspective views of the joining portions of the mounting stand as in FIG. 13;

FIG. 14 is a rear view of the embodiment as in FIG. 9;

DETAILED DESCRIPTION OF THE PREFERRED EMBODIMENTS

FIGS. 1–8 depict a method and apparatus for promoting personal relaxation, for reducing physical and/or psychological personal stress, and/or for expediting personal recovery, such as before, during and/or after a stressful environmental, such as a medical procedure, i.e., surgery.

Figure 1:
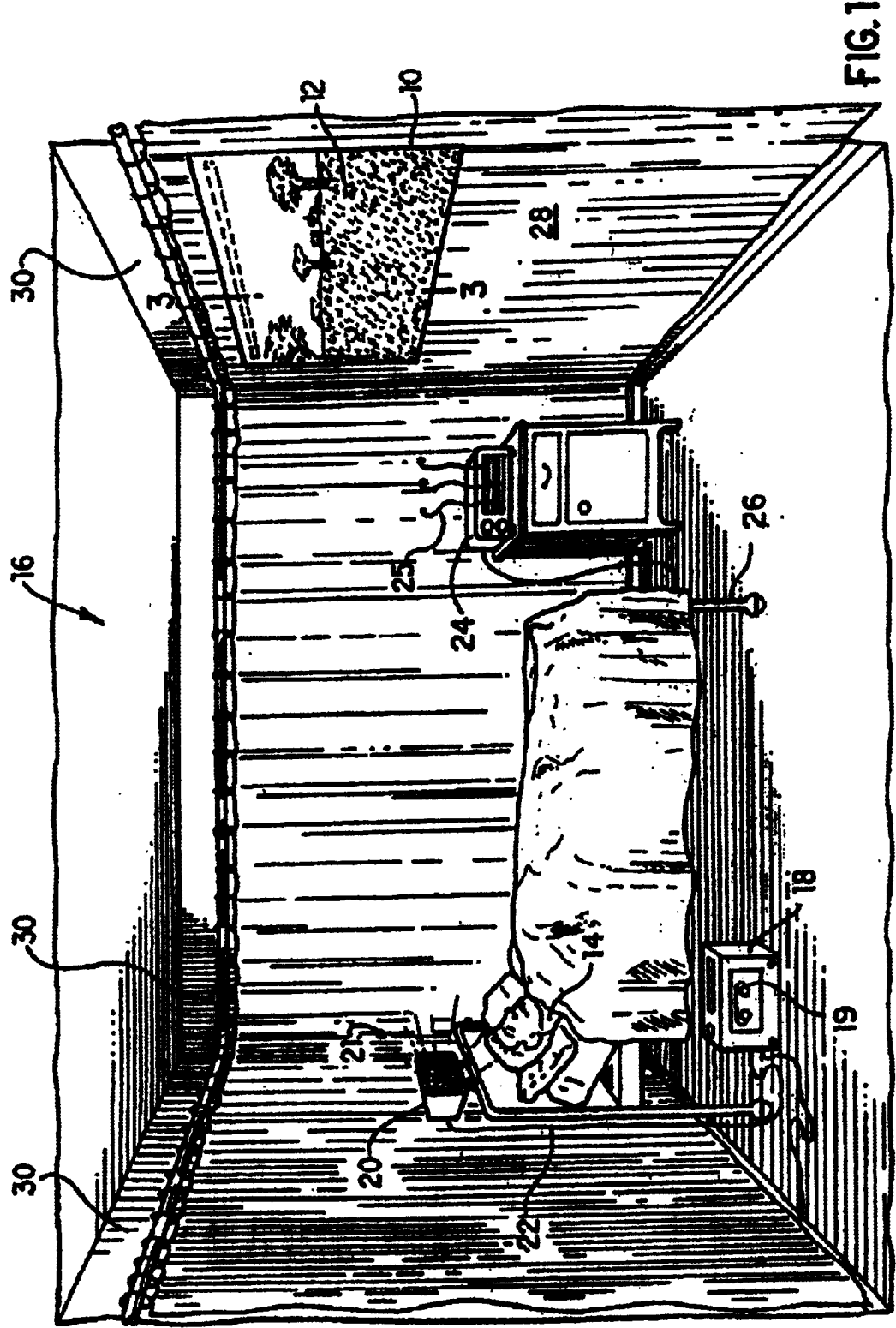
FIGS. 1 and 1A are perspective views of hospital room settings of two embodiments of the method of biophilically enhancing patient welfare.
Figure 1A:
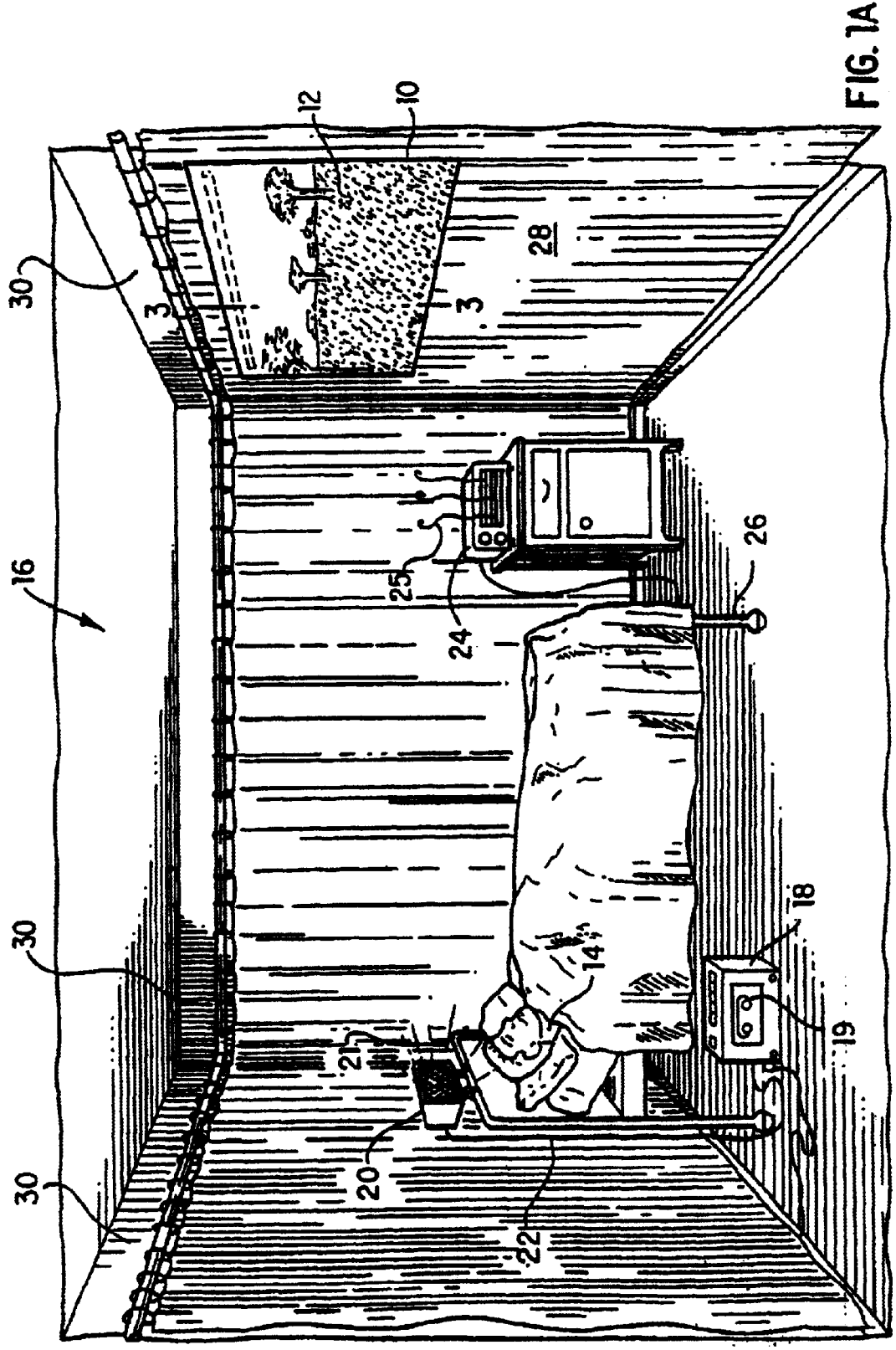

FIG. 1 shows biophilic picture display 12 being draped from a curtain rod. FIG. 1A shows biophilic picture display 10 being attached to a curtain by hook and loop VELCRO® fasteners.

The preferred method includes the steps of providing a changeable visual display device 10, 40, 50, 70 or 80 for displaying one or more appropriately selected spatially open, serene pictorial natural landscape pictures 12, 42, 52, 72 or 82 for which a person 14, 74 or 84, has a predisposed affinity. Preferably, a biophilic picture such as picture 12, 42 or 72 is utilized. Other spatially open, serene natural landscape pictures, with specific landscape physiognomy criteria, such as picture 52 may also be used.

In FIGS. 1 and 1A, changeable visual display devices 10, such as a photomural, are provided in a facility associated with performance of surgical procedures, such as hospital room 16. Changeable visual display devices 10 are used to visually expose predetermined person 14 to one or more appropriately selected spatially open natural landscape pictures, such as biophilic picture 12, printed on display device 10, which display device 10 is substantially optically glare-free and removably attachable to a structure, such as hospital curtain 28, before, during and/or after performance of surgery or other medical procedures on person 14.

Figure 7:
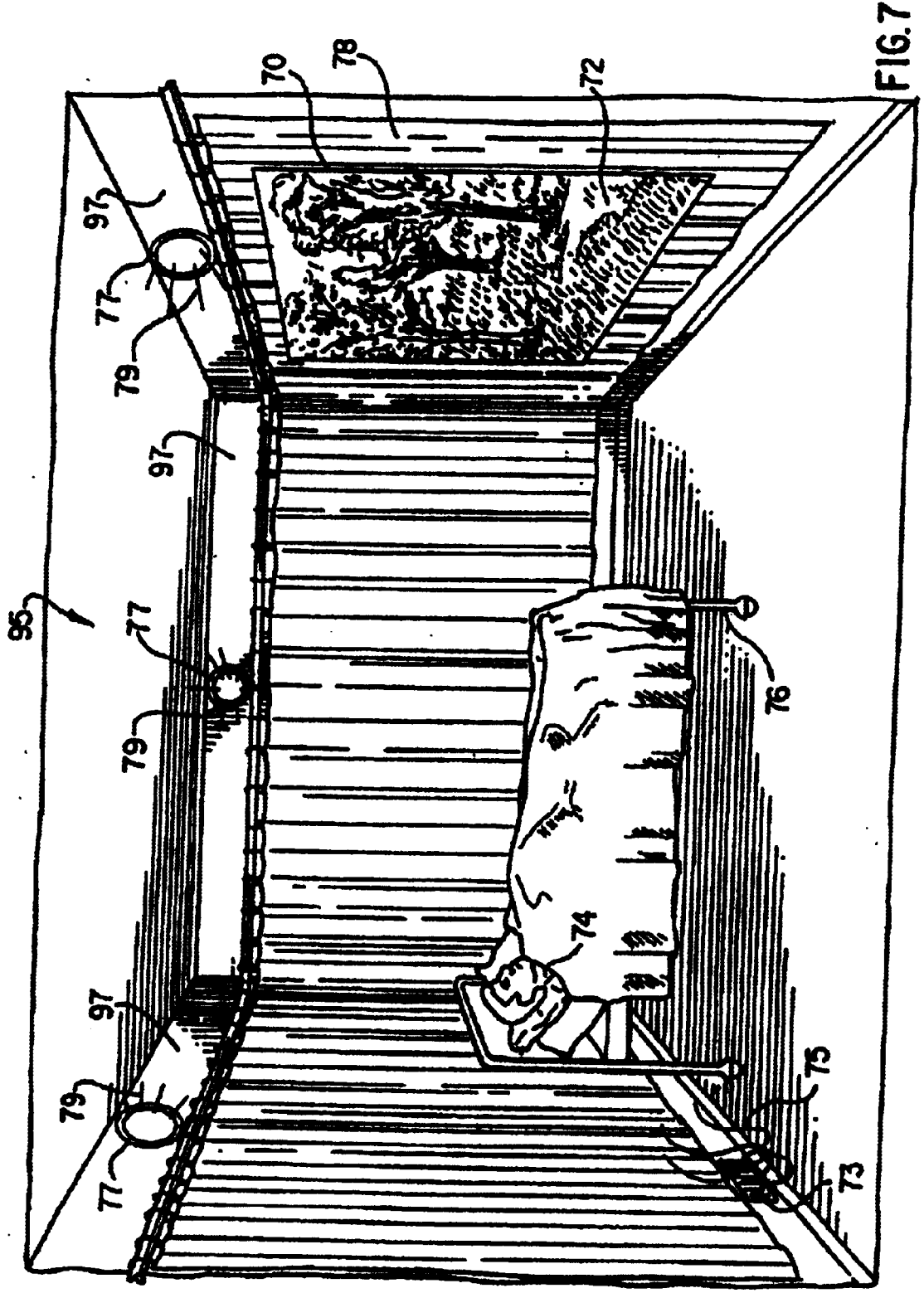
FIG. 7 is a perspective view of a hospital room setting of another embodiment of the present invention, showing a larger biophilic landscape image on a flexible fabric display.

Alternatively, as shown in FIG. 7, the visual display 70 of biophilic picture 72 may be large, such as four feet in height by five feet in width or larger, and may take up a substantial portion of viewing portion of hospital curtain 78 in room 95, so that person 74 may concentrate on viewing biophilic image 72 without eyestrain produced by distant wall-mounted pictures or large, glare producing lighted images from light boxes or other electronic video screens. Moreover, the entire curtain may have a biophilic picture printed directly thereon.

Figure 8:
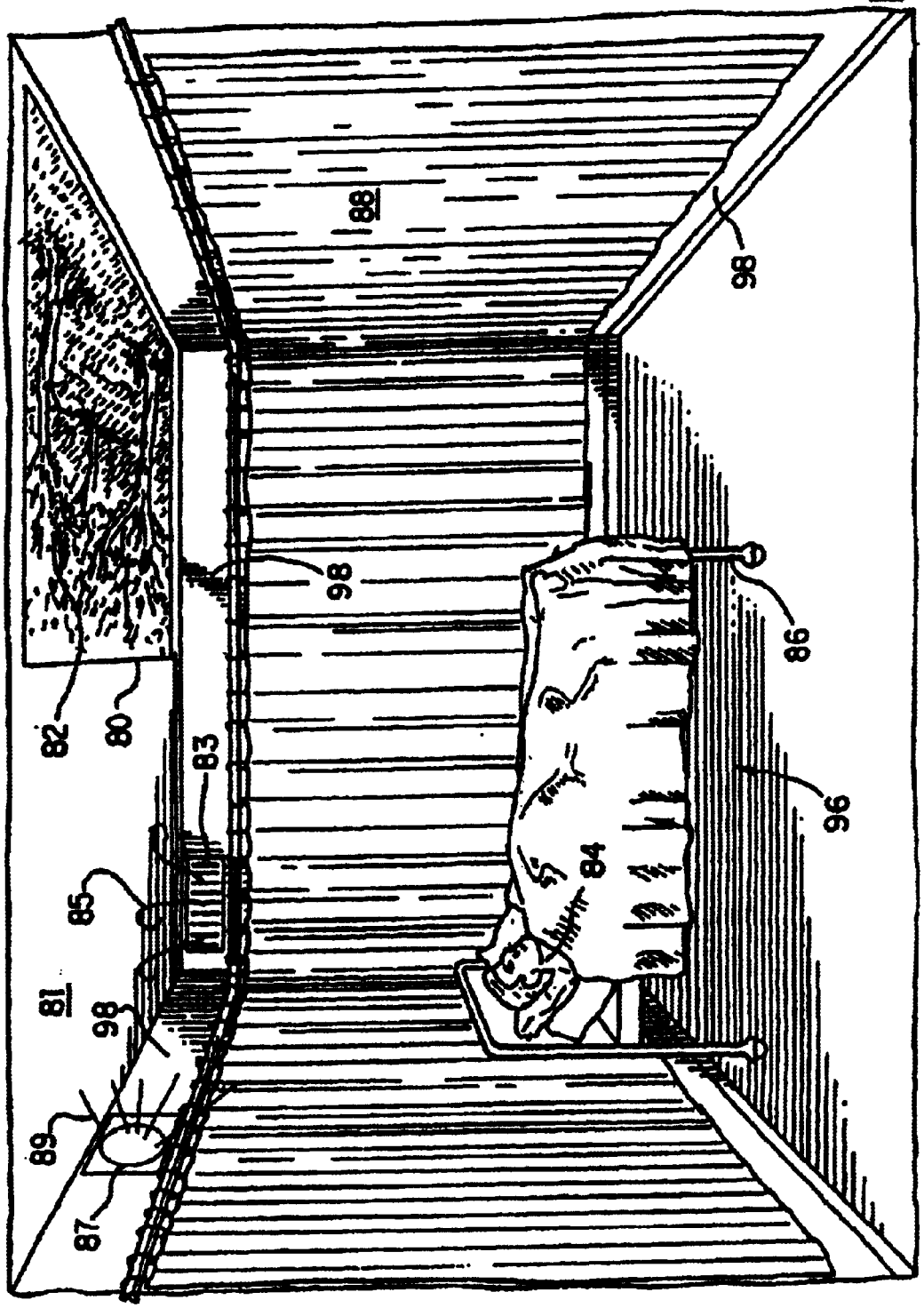
FIG. 8 is a perspective view of a further alternate embodiment of the present invention, showing a ceiling mounted biophilic landscape image.
Figure 9:
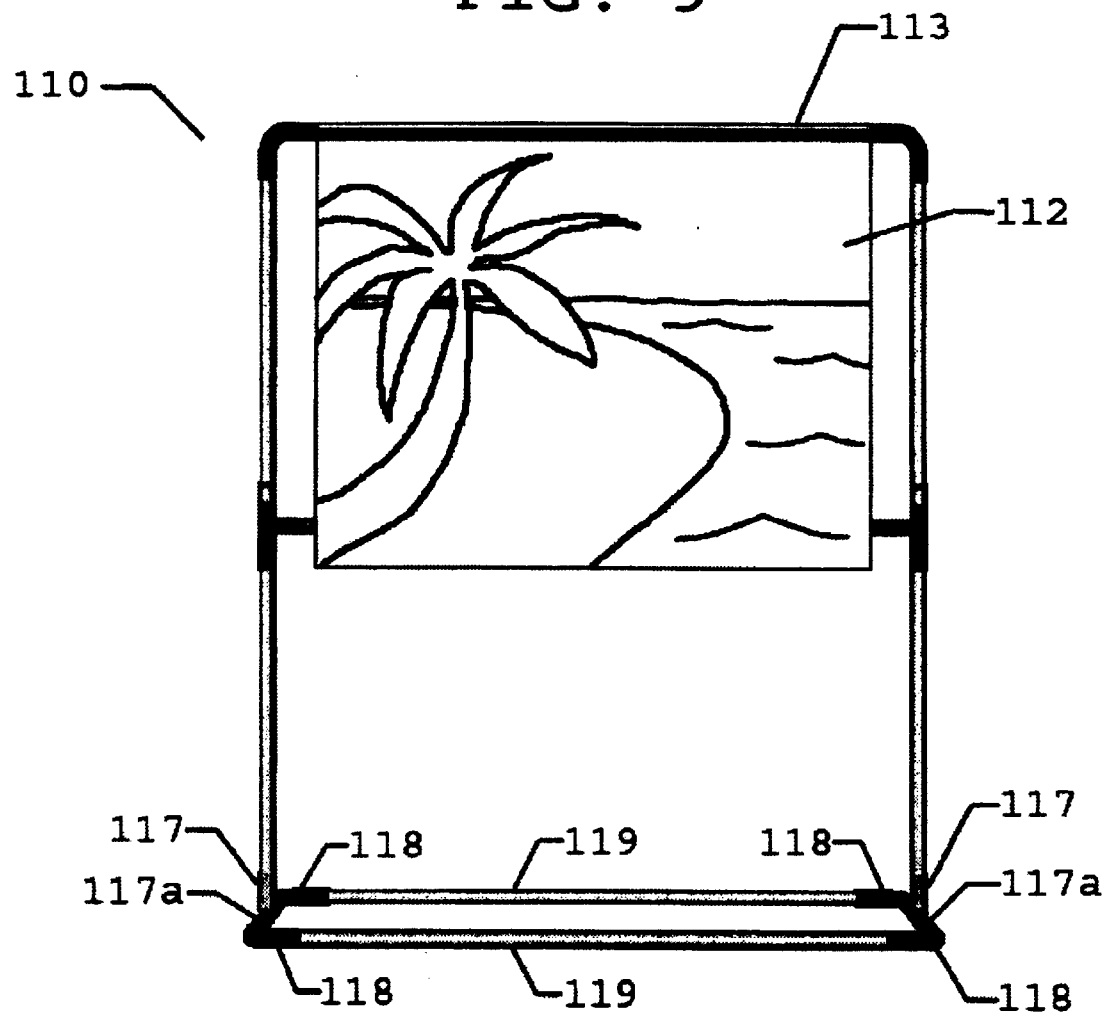
FIG. 9 is a front perspective view of a still yet further alternate embodiment for a biophilic landscape image display mounted upon a self standing support stand.
Figure 10:
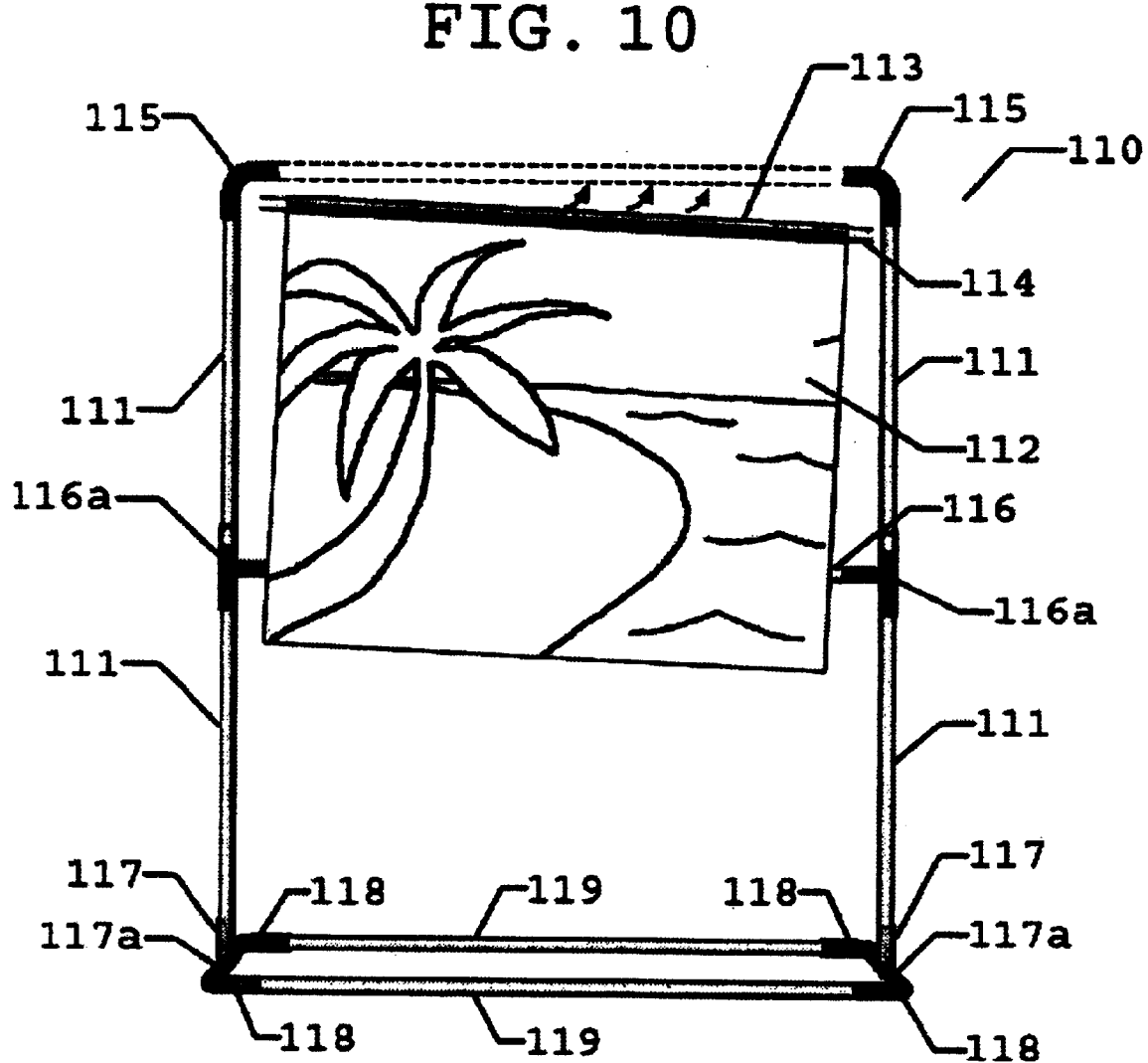
FIG. 10 is a front perspective view of the embodiment shown in FIG. 9, showing the mounting of the biophilic landscape image display by the arrow indicated therein.
Figure 11:
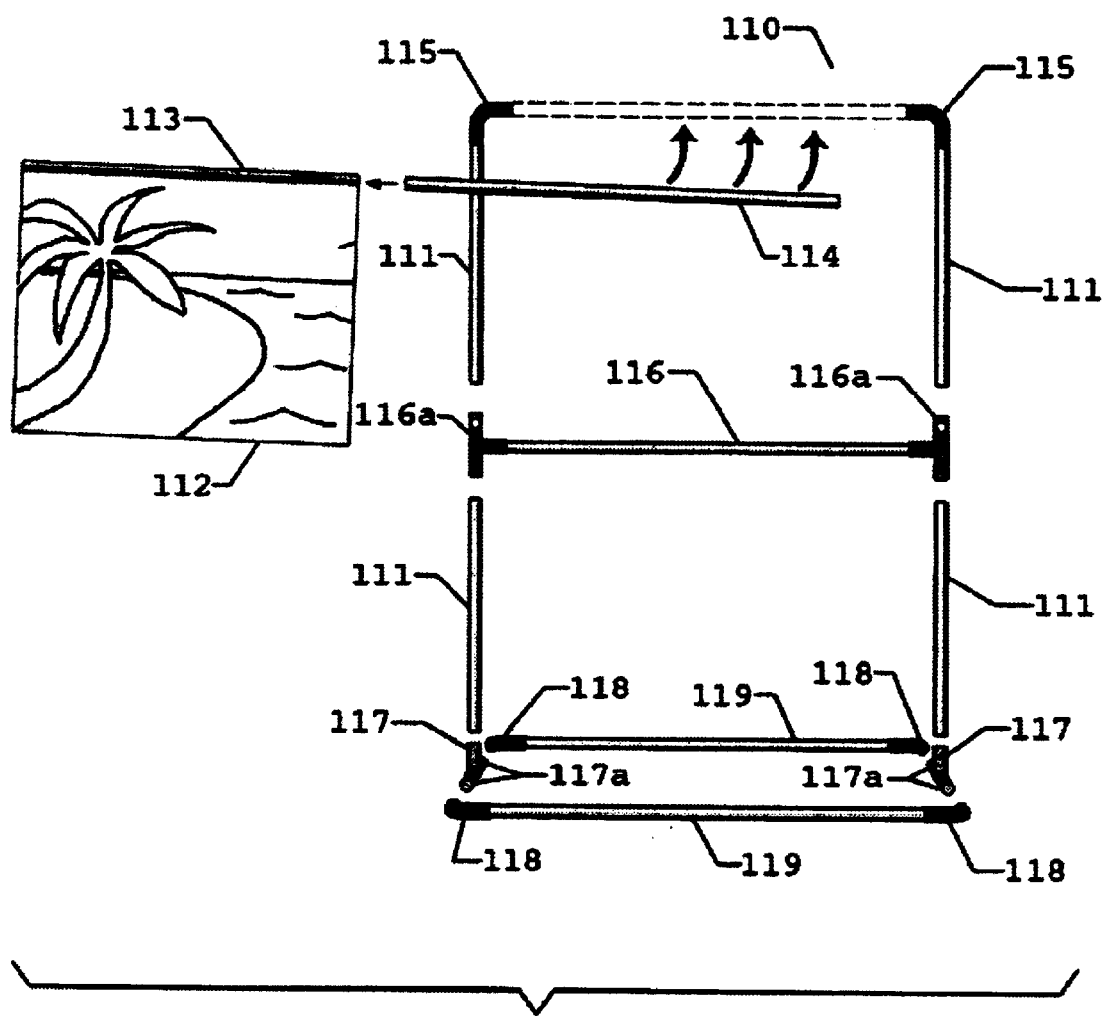
FIG. 11 is an exploded perspective view of the embodiment as in FIG. 9.
Figure 12:
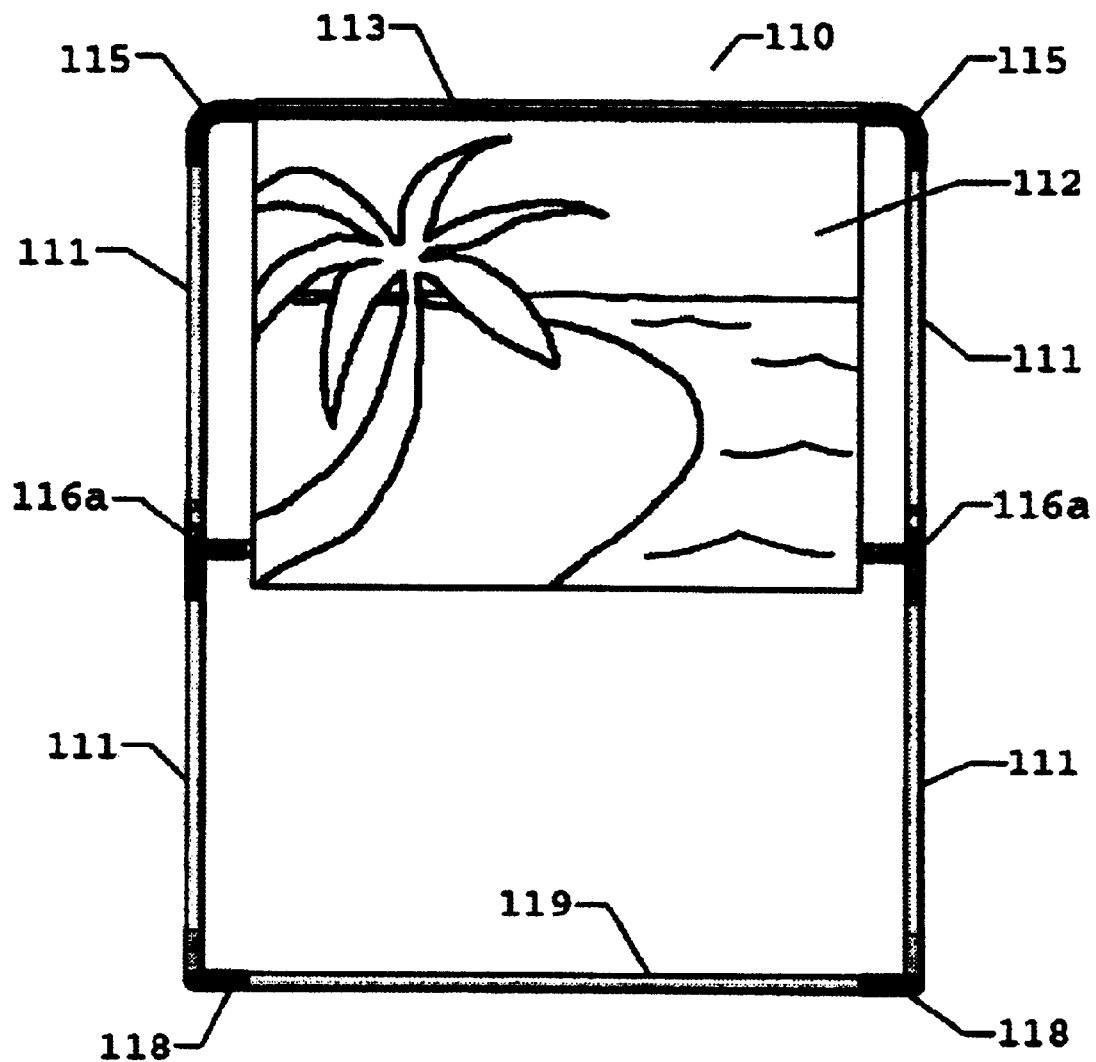
FIG. 12 is a front elevational view of the embodiment as in FIG. 9.
Figure 15:
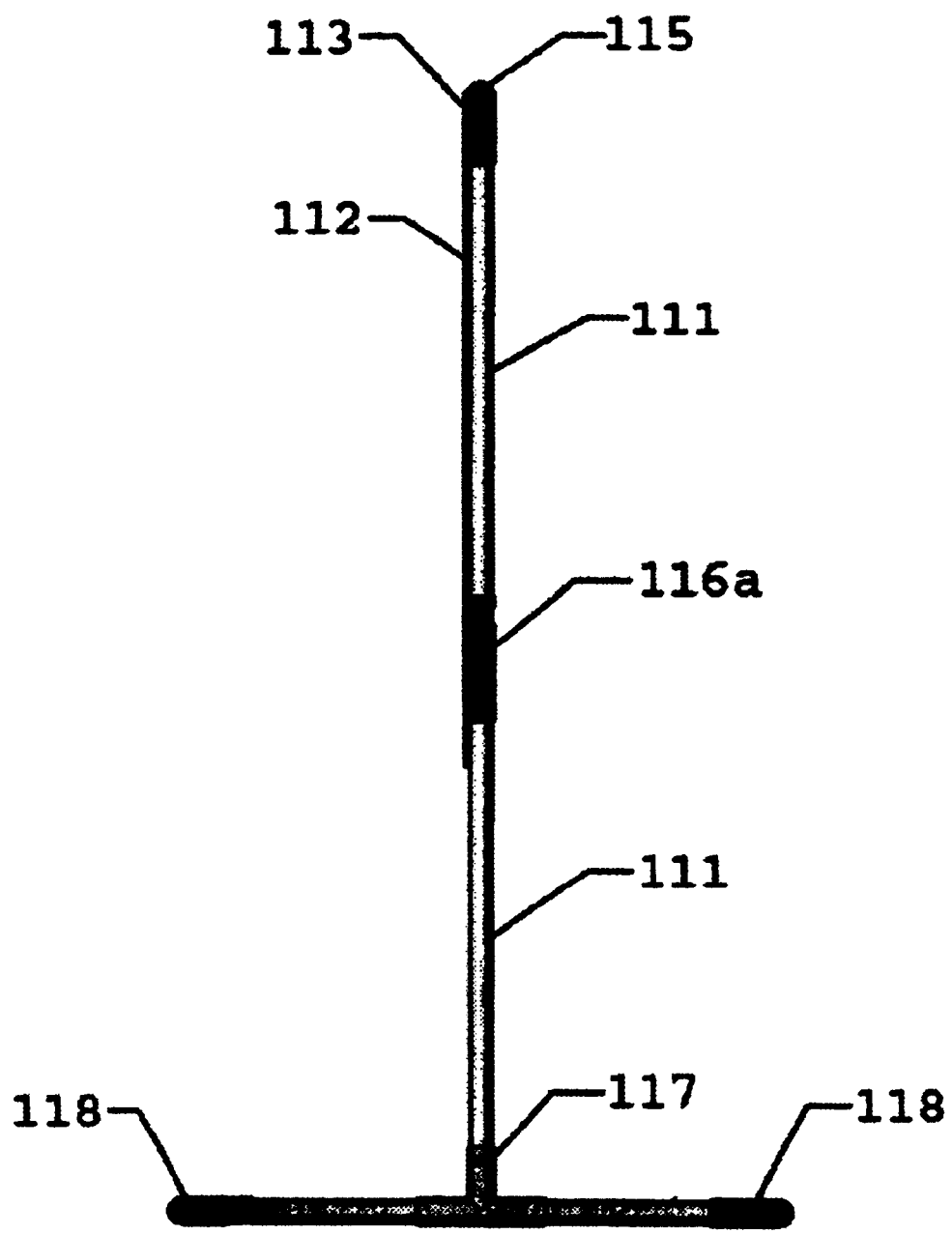
FIG. 15 is a right side elevational view of the embodiment as in FIG. 9.
Figure 16:
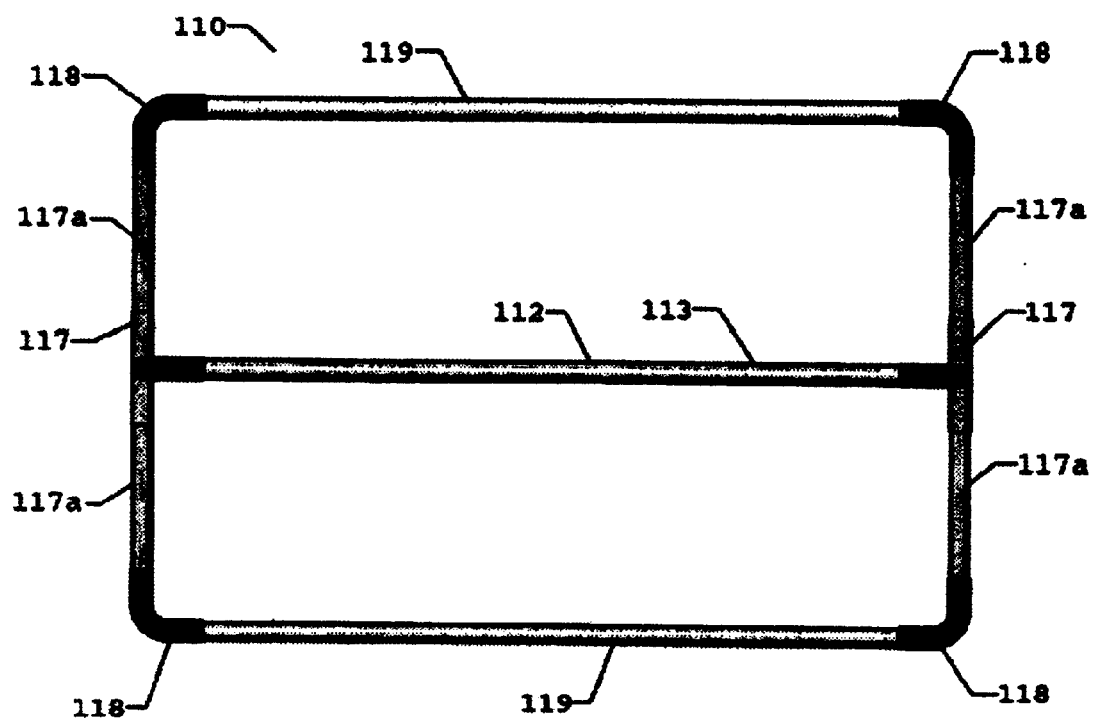
FIG. 16 is a top plan view of the embodiment as in FIG. 9.

As shown in FIG. 8, for persons who are immobilized in a substantially supine position, instead of upon curtain 88, biophilic image 82 upon display 80 may be provided upon the ceiling of room 96.

Furthermore, visual displays 80, such as biophilic photomurals, may be also attached to ceiling panels that fit into standard ceiling metal grids. They can be used as single panels or can used in multiples to simulate biophilic natural scenes on the ceiling of corridors so as to provide the anxiety and stress reduction benefits to patients as they are transported through the hospital corridors. The sounds may be broadcast from a centralized source and heard in each location by means of ceiling or wall mounted speakers or provided to individual patients by means of a personal WALKMAN® type stereo player.

As noted before, patients are routinely transported through hospital corridors, going to and from diagnosis, treatment and surgery. These are usually times of intense anxiety and stress for the patients. These states of psychological distress have been shown to suppress immunological functioning and thereby hinder the patients' physiological recovery. Therefore, display 80 provides patients with relief of this distress during these critical moments of transport.

These biophilic ceiling healing environments can alternatively be used on the ceilings of any healthcare setting e.g. patient rooms, procedure rooms, diagnostic rooms, emergency, operating rooms, etc. They may also be used in elevators.

As respectively shown in FIGS. 1, 1A, 7 and 8, person 14, 74 or 84 is visually exposed to at least one visual picture, such as biophilic image 12, 72 or 82 upon visually proximate and substantially glare-free display device 10, 70 or 80, as biophilic stimuli for neurologically and biophilically promoting in person 14, 74 or 84 the sequelae effects of relaxation, reduction of physical and/or psychological stress, and/or acceleration of patient recovery time.

Additionally and synergistically, recordings of sounds conducive to causing patient relaxation, such as audio cassette tape 19, (or a compact disc) may be played on audio player device 18, which preferably is a device of the type including audio tape players and compact disc players, through speaker 20, such as amplified speakers, headphone or pillow speakers. Speaker 20 is connected to audio player device 18 by audio-signal-transmitting cable or by suitable wireless communication means or other means, for producing sounds 21.

Playing the sound recordings on audio player device is causes the sounds 21 to be heard by person 14 and augments person 14's exposure to biophilic image 12 of display 10, thereby contributing to biophilic relaxation and ultimate recovery of person 14. The recorded sounds preferably are natural sounds appropriate to the content of biodhilic picture 12. Alternately, audible or subliminal healing promoting verbal suggestions or electronic sounds may be provided in conjunction with the viewing of the subject matter of biophilic picture 12 upon flexible display 10 mounted to curtain 28 or other suitable mounting means.

FIGS. 7 and 8 respectively show sounds 79 or 89 entering hospital rooms 95 and 96 through speakers 77 or 87 upon respective walls 97 or 98, from remotely located audio player devices.

As shown in FIG. 1, further additionally and synergistically therapeutic aromatic vapors 25 may be optionally emitted from aromatic vapor dispenser 24 so as to argument the positive effect of viewing of biophilic picture 12 by patient 14. Alternatively as shown in FIGS. 7 and 8, respective aromatic vapors 75 and 85 may be emitted through respective vents 73 and 83 from sites remote from respective rooms 95 and 96.

Visual display device 10, which contains biophilic picture 12, is removably mounted on, or in front of, a structural surface, such as hospital curtain 28, substantially near patient 14 supported in an article of furniture 26, such as a bed, in a room, such as in hospital room 16. Biophilic picture 12 is strategically situated in a stressful environment, such as room 16 so that person 14 can comfortably view biophilic picture 12 substantially without distraction and in an substantially glare-free environment. The presence of hospital curtain 28 helps prevent or reduce such distraction from nonbiophilic visual sources, such as hospital room wall 30, or from lighted, optically glare-producing light boxes or video screens.

Moreover, additional biophilic pictures may be provided on other viewable portions of curtain 28, such as to the left or right side of person 14.

Figure 2:
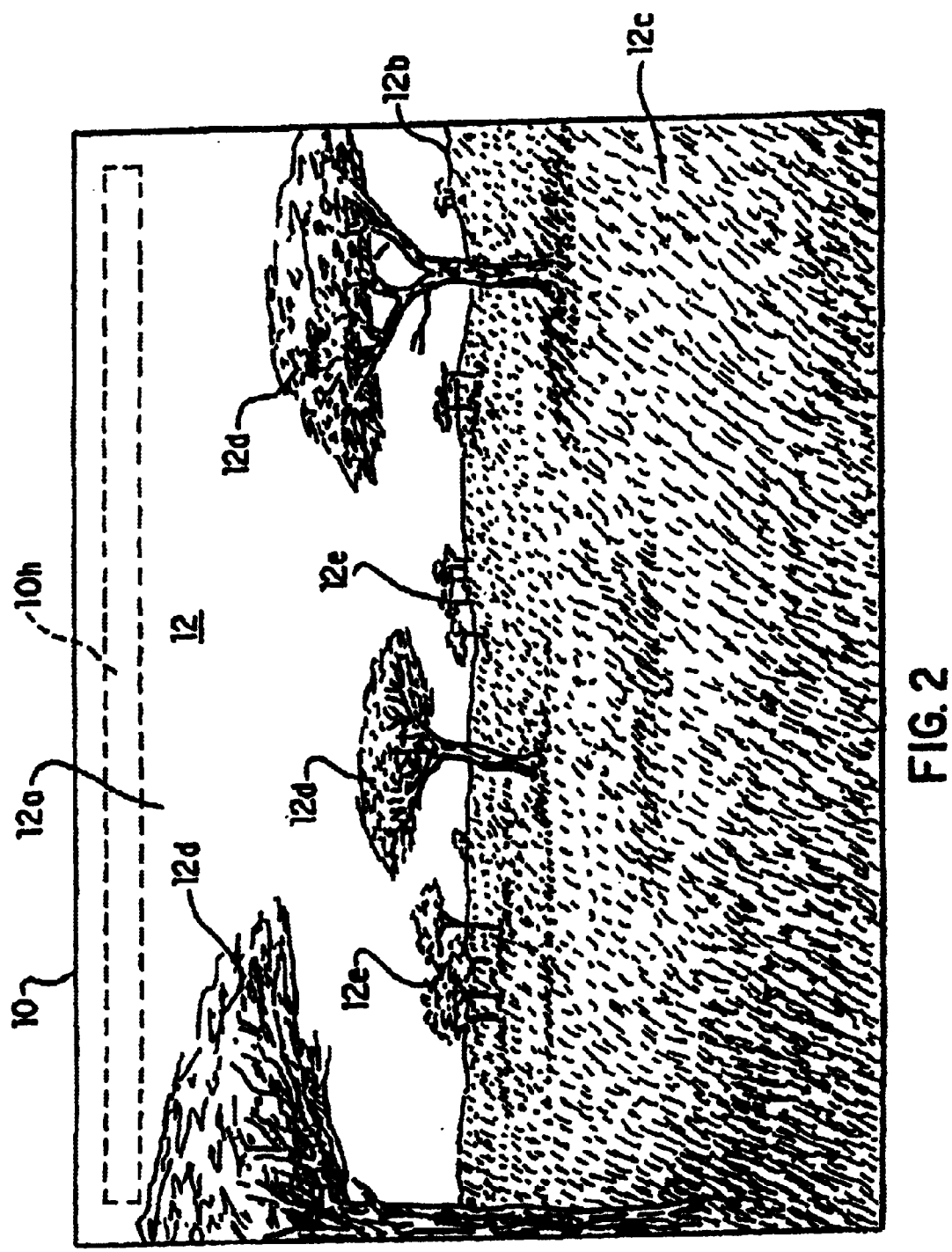
FIG. 2 is a front elevational view of a biophilic landscape image on a flexible fabric display used with the method and apparatus of FIGS. 1 and 1A.

As shown in FIG. 2, preferred biophilic picture 12 depicts a savanna-type landscape scene. Biophilic picture 12 is appropriately selected from a scrutinized set of pictures, and includes a wide, preferably blue, sky portion 12a beginning along and extending above distant horizon line 12b. Horizon line 12b separates sky portion 12a from savanna-type vegetation comprising substantially herbaceous understory of plant life 12c (preferably grasses, sedges and the like) under a relatively open canopy formed by substantially widely spaced trees 12d, and/or tree clusters 12e.

Figure 5:
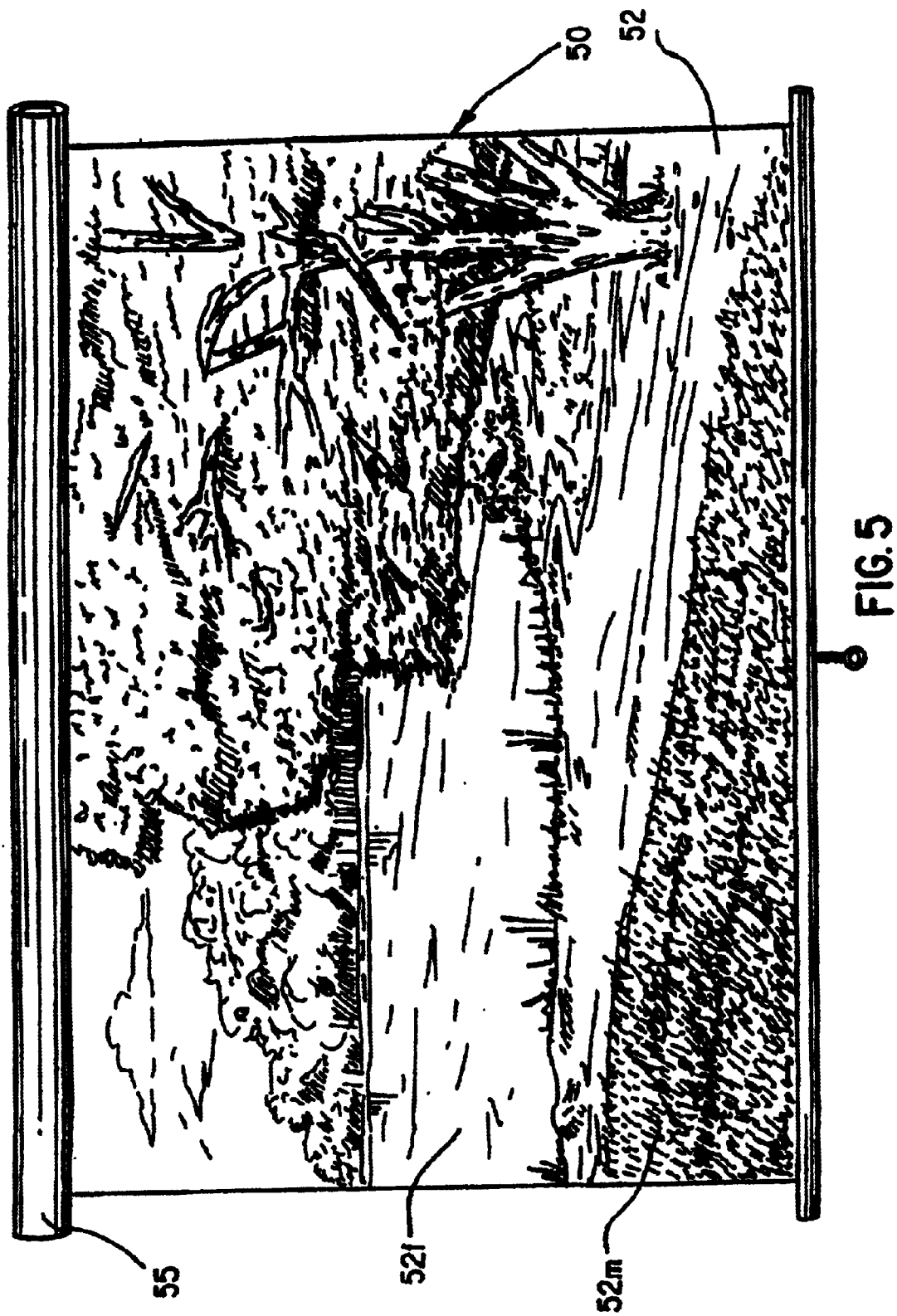
FIG. 5 is a front elevational view of a roll-up-able and roll-down-able device for displaying a still further spatially open natural landscape imagery including a substantially serene hydric feature.

Although depiction of water is not shown in the preferred embodiment of FIGS. 1, 1A and 2, in the alternative, FIG. 5 shows display device 50 of shade-like material 52m with picture 52 including a spatially open natural landscape and tranquil water body 52f.

To prevent or reduce undesirable stimulation of the imagination or the balance of person 14, negatively exciting or anxiety producing landscapes are avoided in selecting biophilic picture 12. In addition, distracting 10 display means, such as optically glare-producing video screens are avoided.

As noted previously, according to Ulrich and Wilson, human beings are believed to be genetically pre-disposed to favor views of savanna-type scenes with a particular vegetation physiognomy, such as shown in biophilic picture 12, because the environmental scene shown therein resembles savanna-type landscape conditions under which natural selection pressures promoted evolutionary differentiation of the genus Homo from paleoanthropoids.

Therefore, appropriate standards of selecting landscape scenes with particular vegetation physiognomy are used to narrow the field of the appropriate pictures to choose from.

Figure 3:
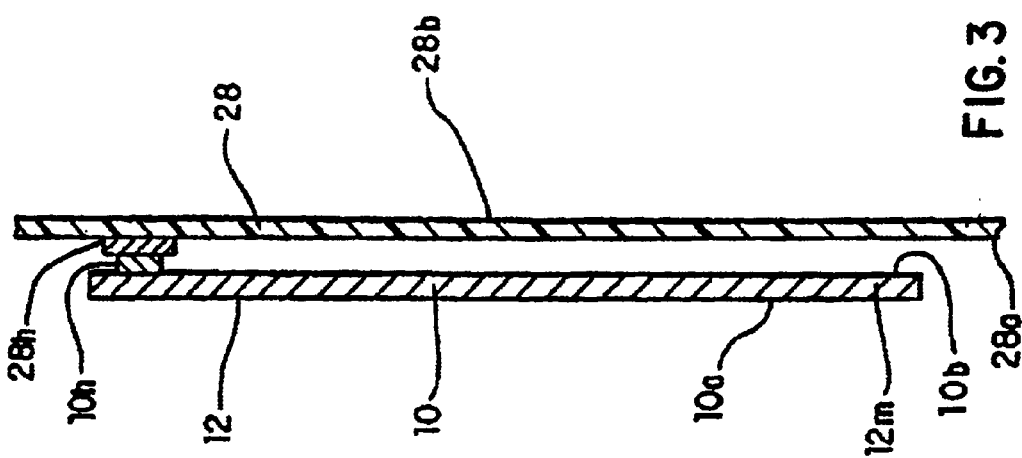
FIG. 3 is a side elevational view in cross-section of the flexible fabric display shown in FIG. 1A.

With respect to the embodiment shown in FIG. 1A, as also shown in FIG. 3, display device 10 displays, on front side 10a, biophilic picture 12 printed on fire retardant flexible panel of fabric material 12m. Rear side 10b of display device 10 is attached to curtain 28 by conventional fasteners, such as hoop-and-loop fastener 10h, corresponding to hook-and-loop fastener 28h attached to front side 28a of curtain 28, which curtain 28 can be made of fabric or synthetic resins. Alternatively, fastener snaps pins (not shown) or other fastener devices may be employed to attach a display device to a flexible curtain, such as curtain 28, or another kind of structure, (such as ceiling 81 or movable partition 88 in hospital room 96, shown in FIG. 8) or a wall or other like structure.

If a person is convalescing at home without a hospital curtain, the visual display means may include a picture frame, wherein biophilic picture 12 is mountable in the frame, as long as the size of the picture is increased to provide an intimate, proximate setting of the selected picture in the stressful environment, such as a person's room.

Figure 4:
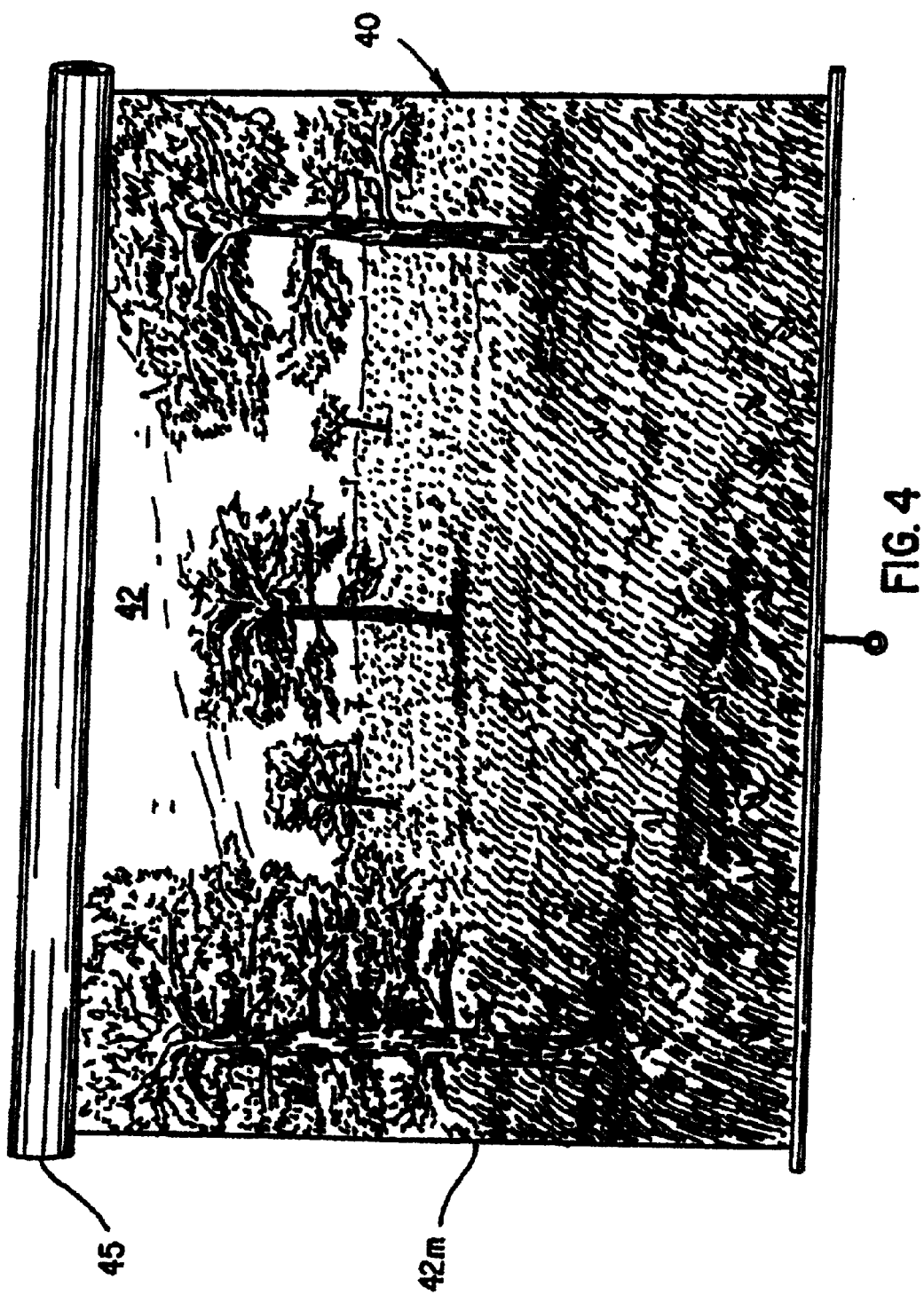
FIG. 4 is a front elevational view of roll-up-able and roll-down-able device for displaying another spatially open natural landscape image.

In the alternative embodiment shown in FIG. 4, display device 40 includes roll-up-able and roll-down-able shade-like material 42m which is substantially rollable about an inner spindle (not shown) within support cylinder 45 wherein spatially open natural landscape picture 42 is adhered to roll-up-able and roll-down-able shade-like material 42m.

In a further alternate display embodiment shown in FIG. 5, display device 50 is also roll-up-able and roll-down-able shade like material 52m, which is substantially rollable about an inner-spindle (not shown) within support cylinder 55, wherein further spatially open, serene natural landscape picture 52, also showing tranquil hydric water body 52f, is displayed on roll-up-able and rolldown-able shade like material 52m.

Figure 6:
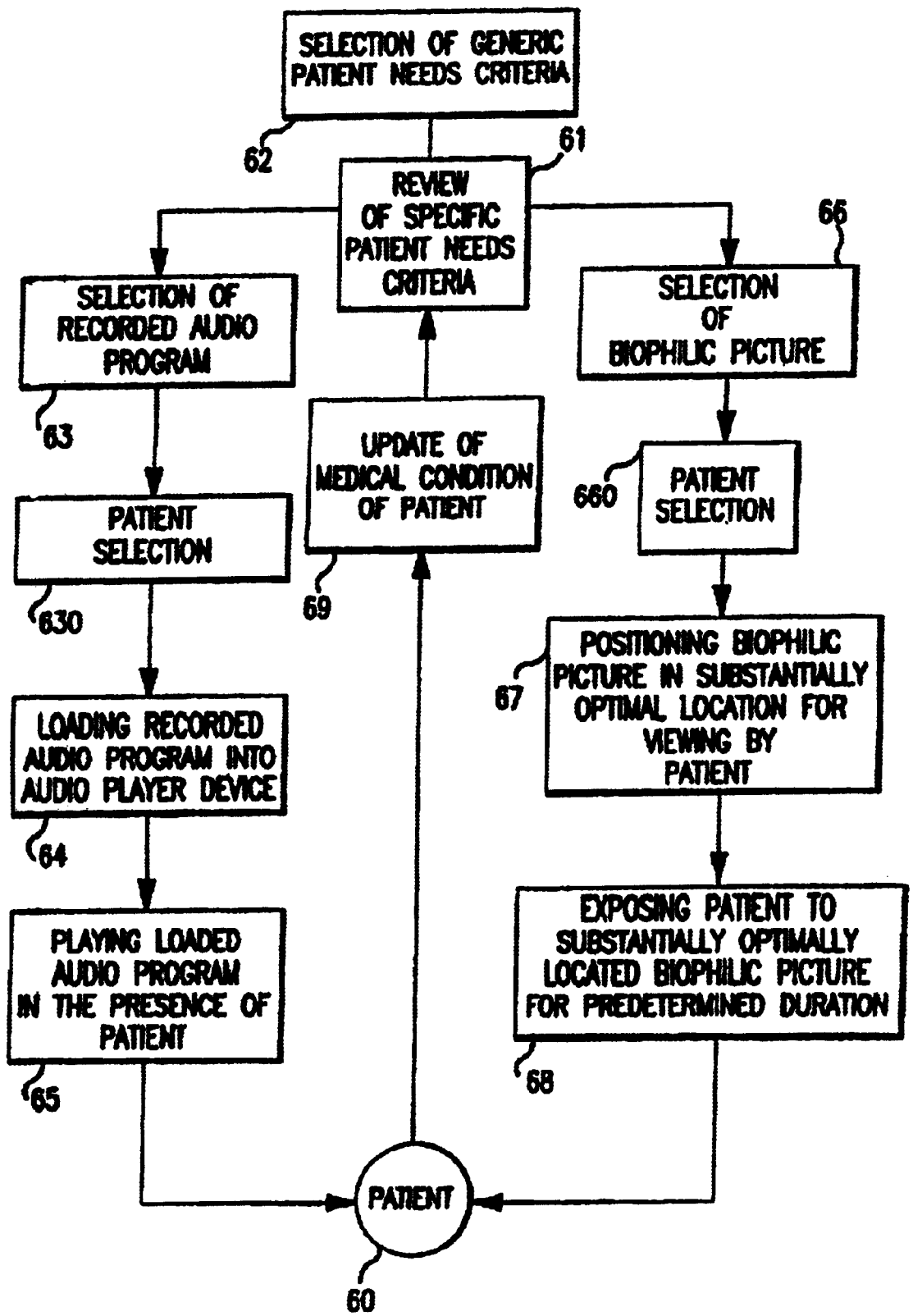
FIG. 6 is a flow chart of an embodiment of the method of the present invention.

FIG. 6 represents a flow chart of the steps of one embodiment of the method of the present invention. In FIG. 6, the person, such as a medical patient, is represented by reference numeral 60. Step 62 represents a care-giver's selection of a distinct, limited set of appropriate visual images or sounds, such as pictures 12, 42, 52, 72 or 82 or sounds 21, 79 or 89 to establish generic patient needs criteria for a variety of patients, such as, for example, person 60. Step 61 involves a comprehensive review of medical condition of a particular patient, such as, for example, person 60, to determine the appropriateness of providing one or more spatially open, serene natural landscapes from the distinct set for viewing by person 60 in an intimate setting. A further selection process includes selecting on parallel tracks the appropriate visual image 66 and related audio program 63 for the person 60.

In the selection process, step 66 involves selecting a visual image, such as biophilic picture 12 by the caregiver, to select a set of a plurality of images (such as pictures 12, 42, 52, 72 or 82) appropriate for person 60. Step 660 of the selection process involves thereafter allowing person 60 to select which image or images person 60 wants to view, if any. The exercise of selecting one or more images 12, 42, 52, 72 or 82 by person 60 is important for bolstering person 60's feeling of self efficacy, which promotes health and well being, and enhances the recovery process.

Similarly, in step 63 for selection of an appropriate audio program, a set of sounds is first selected by the care-giver, and then in step 630 person 60 is given the option of which audio program person 60 wants to hear, or whether or not to hear the audio program at all.

The next steps 64 and/or 67 concern the respective functions of loading the audio program 19 into an audio player device 18 for playing sounds 21, 79 or 89 on speaker 20 to person 60 and the appropriate positioning of picture 12, 42, 52, 72 or 82 in a substantially optimal location and in a substantially glare-free optical environment for viewing by person 60.

The respective final steps 65 and/or 68 include playing the loaded audio program 19 to person 60 through player 18 and speaker 20, in conjunction with exposing person 60 to picture 12, 42, 52, 72 or 82 for a period of time.

As shown in FIG. 6, the process is periodically renewed, since the medical condition of person 60 is updated in step 69. Therefore, in step 61 person 60's needs criteria are periodically reviewed and updated. Moreover, the exercise of choice by person 60 in the selection steps 630, 660 is updated as well, so that person 60 can terminate either the playing of audio program 19 and/or the viewing of picture 12, 42, 52, 72 or 82 at will.

FIGS. 9–16 show a still yet further alternate embodiment for a biophilic landscape image display mounted upon a self standing portable support stand 110. The visual image, such as biophilic picture, such as photomural 112, includes a hollow sleeve portion 113 at a top edge thereof, into which hollow top sleeve is inserted support rod 114.

Support rod 114 is itself insertable within hollow J-shaped joints 115 at either end thereof, which together with rod 114 form a top horizontal support member for self standing support stand 110 having vertical post members 111 attached by T-shaped joints 116 to cross brace 116. The stand 110 is self supporting by virtue of its base, which includes "T"-shaped members 117 having extension sleeves 117a, to which hollow extension members 117a are attached "J"-shaped corner pieces 118, pairs of which are joined by horizontally lying brace members 119. In this application the photomural is hung from portable stand 110 by inserting removable top horizontal rod 114 through a sleeve which runs across the top of the photomural 112.

Portable stand 110 is placed in direct line of sight of the person, usually at the foot of a patient's article of furniture, such as a bed, gurney or recliner. Alternatively, for patients who are receiving chemotherapy, dialysis or other treatment where they are side by side with other patients, portable stand 110 can, by being placed at the patient's side, serve as a privacy screen between patients.

Portable stand 110 adds considerable flexibility of use for both institutional as well as home healthcare and home stress reduction applications.

For institutions, portable stand 110 allows the staff to utilize this biophilic environment for multiple patients on an "as needed" basis. Portable stand 110 is lightweight and is easy for a single staff person to transport. This portability makes it easy, for example, for a staff person to bring visual display 112 directly to a patient who is anxious and is having difficulty falling asleep in order to relax that patient and, thereby, assist them in failing asleep.

Optionally, portable stand 110 may have audio player 120 either built-into portable stand 110, such as within one or more of its components, for example within one or more joining members 116a, or else audio player 120 may be affixed thereto by an attaching means, such as a clip, support hook or anti-theft cable for a removable audio player (not shown). Furthermore, portable stand 110 may optionally have aroma dispenser 121 built-in or affixed thereto.

Portable stand 110 with visual display 112 allows institutions to also flexibly respond to the needs of specific populations of patients. For example, portable stand 110 allows the staff to use it, as an early intervention against the use of physical and pharmacological restraints, or to distract and relax Alzheimer's patients who are exhibiting "catastrophic reactions."

Portable stand 110 allows institutions to provide the stress reducing benefits of the biophilic environment in settings where there are no appropriately located existing cubicle curtain tracks to hang it from, or where the position of the existing tracks is not ideal for optimal viewing by the patient, e.g. for bathing, hydrotherapy, occupational, physical therapy and other rehabilitation, intensive care (ICU's, CCU's), or within private rooms, waiting rooms, conference, meeting or quiet, meditative rooms for family/physician conferences or personal reflection and repose, etc.

For use in private residential homes, such as for convalescence, long-term care, palliative(or hospice) care, treatment and general "well-person" stress reduction, portable stand 110 can display specific biophilic and other therapeutic visual materials of visual display 112 for the needs of particular populations, e.g. Alzheimer's patients, depressed individuals (e.g. whose therapeutic needs may be for stimulation and inspiration) or pediatric patients, wherein portable stand 110 is used to stimulate infant's cognitive development. Also, use of visual display 112 with portable stand 110 may reduce the need for chemical or physical restraints for institutional patients.

Figure 17:
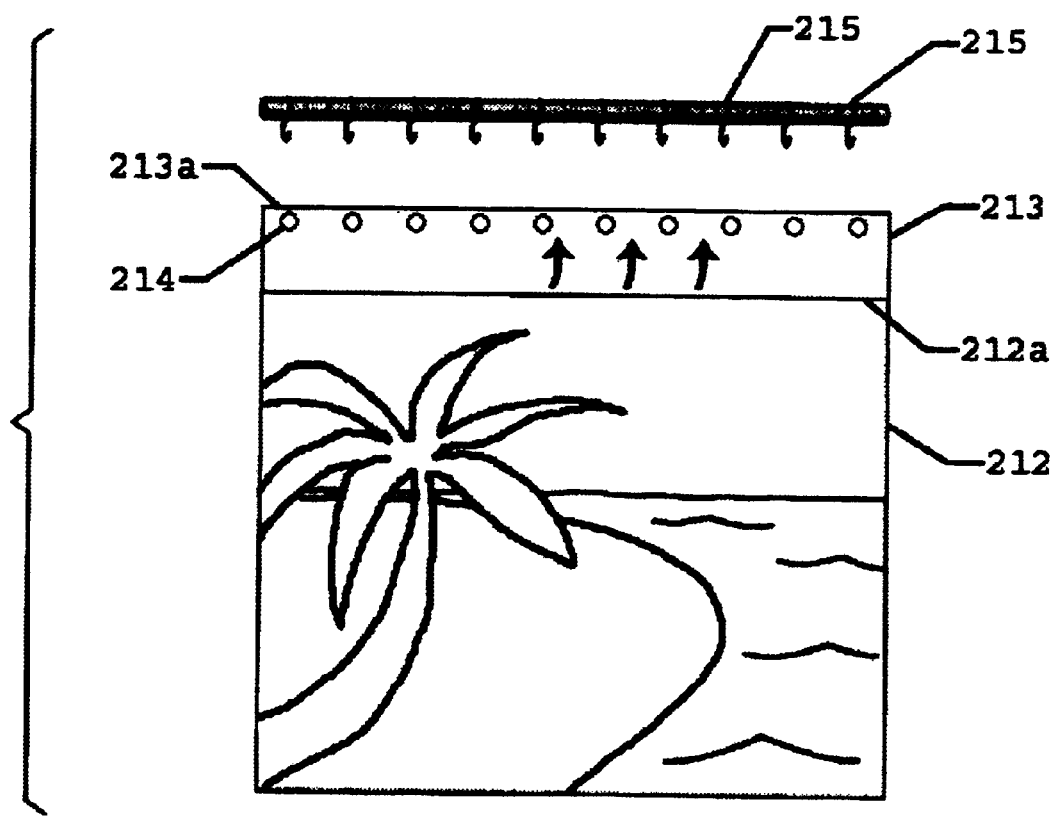
FIGS. 17 and 17A are perspective views of yet other embodiments for a grommet and hook installations for the biophilic landscape image display; and, FIG. 18 is a perspective view of an office mounted environment for the biophilic landscape image display, shown mounted upon an office partition.
Figure 17A:
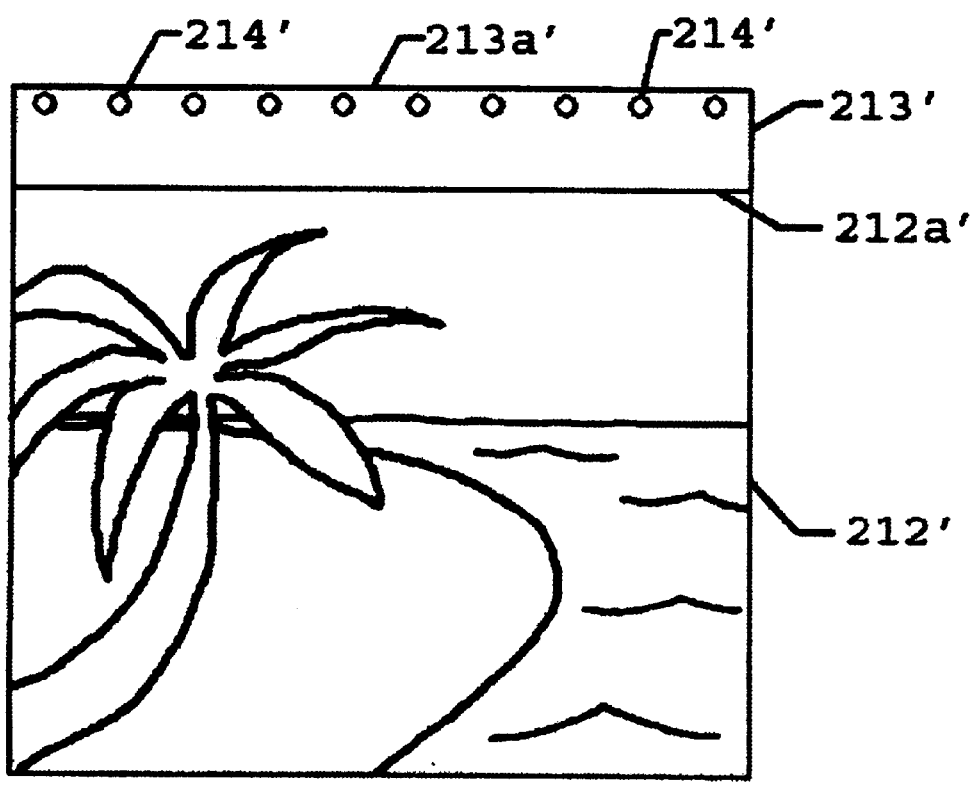

FIGS. 17 and 17A disclose grommet and hook installations for biophilic landscape image displays 212 or 212', similar to that shown in FIG. 1. In FIGS. 17 and 17A, respective flanges, such as mesh flanges 213 or 213', are attached at respective top ledges 212a, 212a' of visual displays 212, 212'.

Eyelet grommets 214, 214' are provided at selected locations along top edges 213a, 213a' of respective mesh flanges 213, 213' for insertion of curtain rod pins therein, such as curtain rod pins 215 of FIG. 17.

Typically, these embodiments shown in FIGS. 17 and 17A includes large (e.g. 42"×52") visual displays 212, 212', such as a biophilic photomural, which have respective sections of hospital curtain-type mesh 213, 213' sewn to top edge portions 213a, 213a' of displays 212, 212' and which displays 212, 212' then are draped over existing cubicle curtains via grommets 214, 214', such as eyelets, button holes or similar devices. These embodiments shown in FIGS. 17, 17A allow visual displays 212, 212' to be hung in direct view of a person, such as patient 14 in FIG. 1, using existing conventional hardware in a room, such as a hospital or other healthcare facility room. It offers the facility two advantages over the hook and loop VELCRO® mounted application shown in FIGS. 1A and 3. For example, using mesh flange 213 or mess flange 213' on top if visual display 212 or 212' does not require any prior preparation of the existing curtain in order to receive visual display 212 or 212', such as a biophilic photomural, since there is no need for sewing of VELCRO® into hospital curtain 28. In addition, because the visual display 212 or 212' are attached higher up and closer to the ceiling, they are less likely to be stolen.

Figure 18:
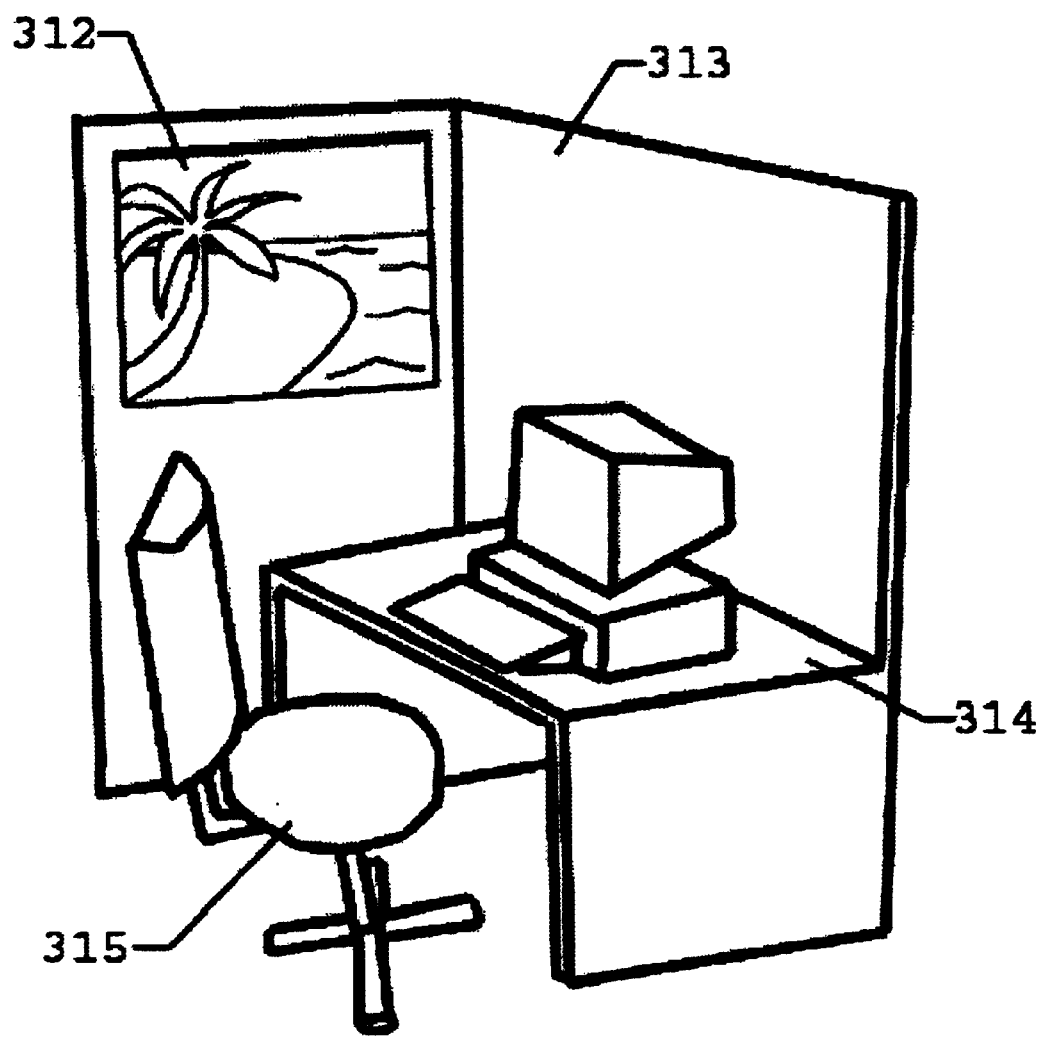
FIG. 18A is an alternate embodiment for the embodiment shown in FIG. 18, where a landscape image display is shown printed directly upon a curtain.

FIG. 18 shows an office mounted environment for the biophilic landscape image display 312, shown mounted upon a support structure, such as office partition 313, before a desk 314 and an article of furniture, such as chair 315, of an office worker in a business office and other public setting, such as in work areas, meeting rooms, cafeterias, employee lounges, hospitality accommodation, such as a hotel lobby or room, where a person is supported in an article of furniture, such as a chair or a bed, etc.

Figure 18A:
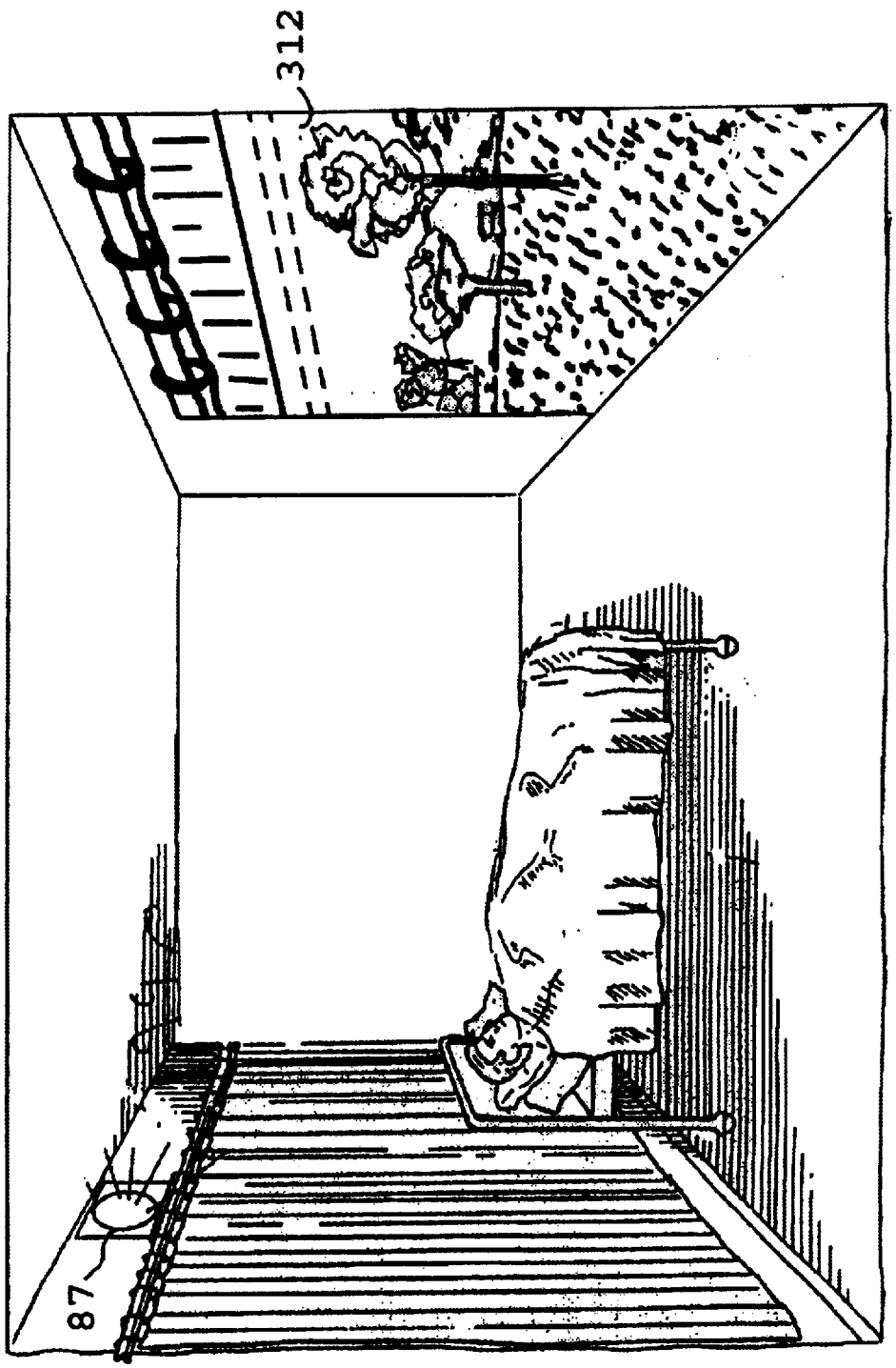

In the office settings shown in FIG. 18, as well as in waiting rooms or hospitality accomriiodations of all types, the biophilic environment visual display 312 can alternately be installed by mounting visual display 312 on a simple curtain rod attached to a wall or partition, as shown in FIG. 18A, similar to rod 114 of the portable mounting stand described in FIGS. 9–16 herein. Visual display 312 is hung in this manner by sliding the rod through a sleeve across a top portion of visual display 312. Auxiliary sounds can be played through a cassette or CD player or broadcast on a channel of an in-house audiovisual system 87.

Visual display 312 with biophilic views, may also be mounted upon modular office dividers/cubicles in the employees'or waiting customers/clients'line of sight (i.e. above the desktops or tops of seating arrangements or along corridors created by such the modular dividers) with or without built-in. (i.e. self-contained) ambient environmental sound devices.

In summary, the present invention includes a method and various apparatus'of biophilically promoting patient welfare, by exposing a person in stressful environments, such as a medical patient in a hospital, to a preferably conveniently mounted, substantially optically glare-free biophilic pictorial landscape image to which human beings are believed to be generally genetically predisposed to viewing favorably, so as to biophilically induce relaxation, reduce stress and/or promote post-surgical recovery. The beneficial effects of providing the landscapes image may be augmented by providing the person with soothing natural sounds or aromas.

Display materials, having a biophilic pictorial landscape image affixed thereto by substantially glare-free high resolution sublimation printing, can be removably or changeably mounted as a convenient removable flexible and lightweight display member, to a hospital curtain or other structure so as to substantially maximize exposure of a person to the biophilic image in an intimate, substantially glare-free environment.

It is also important that the pictures be removable, so that the person can exercise choice in selecting the picture to be viewed, and thereby improve the person's self efficacy and self esteem.

It is also known that other modifications may be made of the present invention, without departing from the spirit and scope of the invention, as noted in the appended claims.

I claim:

1. An apparatus for promoting personal relaxation and reducing stress in an environmentally stressful setting comprising:
    a room containing an article of furniture adapted to support a person;
    said room having a support structure facing said article of furniture within the room;
    a visual display member of fire retardant fabric construction to eliminate glare being suspended from a top edge thereof and hanging freely from said support structure;
    said visual display member being located so that said visual display member is visible in the vicinity of said article of furniture within the line of vision of said person;
    said visual display member having a pictorial display printed directly thereon on a surface facing said person;
    said pictorial display being of a savanna-type landscape containing imagery designed to create relaxation and reduce stress of said person;
    said display being produced on said fire retardant fabric by a high resolution sublimation printing process resulting in said display and said fire retardant fabric being washable and durable to heated washing standards of 160 degrees F. so that any infectious organisms thereon are eradicated;
    means for attaching and permitting ready removal of said fabric visual display member to and from said support structure.

2. The apparatus as claimed in claim 1 wherein said visual display fabric is freely suspended from a curtain rod mounted on a wall.

3. An apparatus for promoting personal relaxation and reducing stress in an environmentally stressful setting comprising:
    a room containing an article of furniture adapted to support a person;
    said room having a wall facing said article of furniture;
    a curtain rod mounted on said wall;
    a visual display curtain member of fabric being suspended from said curtain rod;
    said visual display curtain member being located so that said visual display curtain member is visible in the vicinity of said article of furniture within the line of vision of said person;
    said visual display curtain member having a pictorial display printed directly thereon on a surface facing said person; and
    said pictorial display being of a landscape containing imagery designed to create relaxation and reduce stress of said person.

4. The apparatus as in claim 3 further comprising a sound emitting device providing biophilic sounds.

5. The apparatus as in claim 3 further comprising an aromatherapy emitting device providing aromas.

6. The apparatus as in claim 3 wherein said pictorial display is a landscape of open spaces, interspersed with distinct spread apart elements including trees, to create relaxation and to reduce stress of the viewer.

7. The apparatus as in claim 3 wherein said pictorial display is a landscape containing imagery suggesting environments in which the evolutionary differentiation of *Homo sapiens* from ancestral paleoanthropopids is believed to have occurred,
    wherein further said biophilic landscape imagery includes imagery of vegetation dominated by a relatively low herbaceous understory and a relatively widely spaced tree canopy.

8. The apparatus as in claim 3 wherein said pictorial display includes imagery of vegetation dominated by a relatively low herbaceous understory and a relatively widely spaced tree canopy.

9. The apparatus as in claim 3 wherein said pictorial display is a nature scene comprising a glare free spatially open serene natural setting.

10. The apparatus as in claim 3 wherein said pictorial display is a natural setting including a tranquil water body.

11. The apparatus as in claim 3 wherein said pictorial display is a natural setting including a wide sky portion beginning along and extending above a distant horizon line and vegetation comprising substantially herbaceous understory of plant life under a relatively open canopy formed by at least one of substantially widely spaced trees and tree clusters.

12. An apparatus for promoting personal relaxation and reducing stress in an environmentally stressful setting comprising:

a room containing an article of furniture adapted to support a person;

said room having a support structure facing said article of furniture within the room;

a visual display member of fire retardant fabric construction to eliminate glare being suspended from a top edge thereof and hanging freely from said support structure;

said visual display member being located so that said visual display member is visible in the vicinity of said article of furniture within the line of vision of said person;

said visual display member having a pictorial display printed directly thereon on a surface facing said person;

said pictorial display being of a savanna-type landscape containing imagery designed to create relaxation and reduce stress of said person;

said display being produced on said fire retardant fabric by a high resolution sublimation printing process resulting in said display and said fire retardant fabric being washable and durable to heated washing standards of 160 degrees F. so that any infectious organisms thereon are eradicated;

means for attaching and permitting ready removal of said fabric visual display member to and from said support structure; and means for emitting biophilic sounds to enhance the relaxing effect of said display.

13. The apparatus as claimed in claim 12 wherein said visual display fabric is freely suspended from a curtain rod mounted on a wall.

14. An apparatus for promoting personal relaxation and reducing stress in an environmentally stressful setting comprising:

a room containing an article of furniture adapted to support a person;

said room having a wall facing said article of furniture;

a curtain rod mounted on said wall;

a visual display curtain member of fabric being suspended from said curtain rod;

said visual display curtain member being located so that said visual display curtain member is visible in the vicinity of said article of furniture within the line of vision of said person;

said visual display curtain member having a pictorial display printed directly thereon on a surface facing said person;

said pictorial display being of a landscape containing imagery designed to create relaxation and reduce stress of said person; and, means for emitting biophilic sounds to enhance the relaxing effect of said display.

15. The apparatus as in claim 14 further comprising an aromatherapy emitting device providing aromas.

16. The apparatus as in claim 14 wherein said pictorial display is a landscape of open spaces, interspersed with distinct spread apart elements including trees, to create relaxation and to reduce stress of the viewer.

17. The apparatus as in claim 14 wherein said pictorial display is a landscape containing imagery suggesting environments in which the evolutionary differentiation of *Homo sapiens* from ancestral paleoanthropopids is believed to have occurred, wherein further said biophilic landscape imagery includes imagery of vegetation dominated by a relatively low herbaceous understory and a relatively widely spaced tree canopy.

18. The apparatus as in claim 14 wherein said pictorial display includes imagery of vegetation dominated by a relatively low herbaceous understory and a relatively widely spaced tree canopy.

19. The apparatus as in claim 14 wherein said pictorial display is a nature scene comprising a glare free spatially open serene natural setting.

20. The apparatus as in claim 14 wherein said pictorial display is a natural setting including a tranquil water body.

21. The apparatus as in claim 14 wherein said pictorial display is a natural setting including a wide sky portion beginning along and extending above a distant horizon line and vegetation comprising substantially herbaceous understory of plant life under a relatively open canopy formed by at least one of substantially widely spaced trees and tree clusters.

* * * * *